US008513005B2

(12) United States Patent
Hooper et al.

(10) Patent No.: US 8,513,005 B2
(45) Date of Patent: Aug. 20, 2013

(54) DNA IMMUNOGENIC COMPOSITION COMPRISING A FULL-LENGTH MODIFIED POXVIRUS L1R GENE FUSED TO A TPA LEADER SEQUENCE

(75) Inventors: Jay W. Hooper, New Market, MD (US); Joseph W. Golden, Hagerstown, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 119 days.

(21) Appl. No.: 12/217,584

(22) Filed: Jul. 7, 2008

(65) Prior Publication Data

US 2009/0074792 A1 Mar. 19, 2009

Related U.S. Application Data

(60) Provisional application No. 60/959,927, filed on Jul. 9, 2007.

(51) Int. Cl.
*C12N 15/00* (2006.01)
(52) U.S. Cl.
USPC ........................................ 435/320.1; 435/455
(58) Field of Classification Search
None
See application file for complete search history.

(56) References Cited

U.S. PATENT DOCUMENTS

| | | | |
|---|---|---|---|
| 6,451,309 B2 | 9/2002 | Hooper | 424/147.1 |
| 6,562,376 B2 | 5/2003 | Hooper | 424/489 |
| 6,620,412 B2 | 9/2003 | Hooper | 424/147.1 |
| 7,217,812 B2 | 5/2007 | Hooper | 536/24.1 |
| 7,790,182 B2 | 9/2010 | Hooper | |
| 2002/0114818 A1 | 8/2002 | Schmaljohn et al. | 424/278.1 |
| 2005/0180994 A1 | 8/2005 | Lu et al. | 424/232.1 |
| 2007/0105193 A1 | 5/2007 | Vilalta et al. | 435/69.1 |
| 2010/0323024 A1 | 12/2010 | Hooper | |

FOREIGN PATENT DOCUMENTS

WO PCT/US2008/001847 8/2008

OTHER PUBLICATIONS

Jiankuo et al., Peptide nucleic acid antisense prolongs skin allograft survival by means of blockade of CXCR3 expression directing T cells into graft, J. Immunol. 170(3):1556-65, 2003.*
Esposito et al., Genome sequence diversity and clues to the evolution of variola (smallpox) virus. Science 2006; 313(5788):807-12.
Gubser C, Smith GL. The sequence of camelpox virus shows it is most closely related to variola virus, the cause of smallpox. J Gen Virol Apr. 2002;83(Pt 4):855-72.
Werden SJ, McFadden G. The role of cell signaling in orthopoxvirus tropism: The case of the M-T5 host range protein of myxoma virus. Biochim Biophys Acta Aug. 14, 2007 (epub ahead of print).
Lewis-Jones S. Zoonotic orthopoxvirus infections in humans. Curr Opin Infect Dis 2004 17:81-9.
Parker S, Nuara A, Buller RM, Schultz DA. Human monkeypox: an emerging zoonotic disease. Future microbiology 2007;2:17-34.
Reed KD, Melski JW, Graham MB, Regnery RL, Sotir MJ, Wegner MV, et al. The detection of monkeypox in humans in the Western Hemisphere. N Engl J Med 2004;350(4):342-50.
Lane JM, Goldstein J. Adverse events occurring after smallpox vaccination. Semin Pediatr Infect Dis 2003;14(3):189-95.
Wharton M, Strikas RA, Harpaz R, Rotz LD, Schwartz B, Casey CG, et al. Recommendations for using smallpox vaccine in a pre-event vaccination program. Supplemental recommendations of the Advisory Committee on Immunization Practices (ACIP) and the Healthcare Infection Control Practices Advisory Committee (HICPAC). MMWR Recomm Rep 2003;52(RR-7):1-16.
Bray M. Pathogenesis and potential antiviral therapy of complications of smallpox vaccination. Antiviral Res 2003;58:101-14.
Kretzschmar M, Wallinga J, Teunis P, Xing S, Mikolajczyk R. Frequency of adverse events after vaccination with different vaccinia strains. PLoS Med 2006;3:e272.
McCurdy LH, Larkin BD, Martin JE, Graham BS. Modified vaccinia Ankara: potential as an alternative smallpox vaccine. Clin Infect Dis 2004;38:1749-53.
Coulibaly S, Bruhl P, Mayrhofer J, Schmid K, Gerencer M, Falkner FG. The nonreplicating smallpox candidate vaccines defective vaccinia Lister (dVV-L) and modified vaccinia Ankara (MVA) elicit robust long-term protection. Virology 2005;341:91-101.
Kidokoro M, Tashiro M, Shida H. Genetically stable and fully effective smallpox vaccine strain constructed from highly attenuated vaccinia LC16m8. Proc Natl Acad Sci USA 2005;102:4152-7.
Edghill-Smith Y, Bray M, Whitehouse CA, Miller D, Mucker E, Manischewitz J, et al. Smallpox vaccine does not protect macaques with AIDS from a lethal monkeypox virus challenge. J Infect Dis 2005;191:372-81.
Galmiche MC, Goenaga J, Wittek R, Rindisbacher L. Neutralizing and protective antibodies directed against vaccinia virus envelope antigens. Virology 1999; 254:71-80.
Fang M, Cheng H, Dai Z, Bu Z, Sigal LJ. Immunization with a single extracellular enveloped virus protein produced in bacteria provides partial protection from a lethal orthopoxvirus infection in a natural host. Virology 2006; 345:231-43.
Davies DH, McCausland MM, Valdez C, Huynh D, Hernandez JE, Mu Y, et al. Vaccinia virus H3L envelope protein is a major target of neutralizing antibodies in humans and elicits protection against lethal challenge in mice. J Virol 2005;79:11724-33.

(Continued)

*Primary Examiner* — Deborah Crouch
(74) *Attorney, Agent, or Firm* — Elizabeth Arwine

(57) ABSTRACT

The invention described here encompasses DNA and protein vaccines against poxviruses, and relevant immunogenic compositions, comprising at a minimum a nucleic acid encoding a modified full-length poxvirus L1R gene or its ortholog. The L1R gene is modified so that an endoplasmic reticulum-targeting sequence is operably linked on the 5' end. Preferably the nucleic acid sequences for other poxviruses antigens are also included, such as A33R, B5R and/or A27L. These vaccines and compositions provide improved neutralizing antibody response elicited by molecular poxvirus vaccines, over known vaccines using unmodified L1R.

9 Claims, 14 Drawing Sheets

(56) References Cited

OTHER PUBLICATIONS

Sakhatskyy P, Wang S, Chou TH, Lu S. Immunogenicity and protection efficacy of monovalent and polyvalent orthopoxvirus vaccines that include the D8 antigen. Virology 2006;355:164-74.
Hooper JW, Custer DM, Schmaljohn CS, Schmaljohn AL. DNA vaccination with vaccinia virus L1R and A33R genes protects mice against a lethal orthopoxvirus challenge. Virology 2000;266:329-39.
Hooper JW, Custer DM, Thompson E. Four-gene-combination DNA vaccine protects mice against a lethal vaccinia virus challenge and elicits appropriate antibody responses in nonhuman primates. Virology 2003;306:181-95.
Hooper JW, Thompson E, Wilhelmsen C, Zimmerman M, Ichou MA, Steffen SE, et al. Smallpox DNA vaccine protects nonhuman primates against lethal monkeypox. J Virol 2004;78:4433-43.
Hooper JW, Golden JW, Ferro AM, King AD. Smallpox DNA vaccine delivered by novel skin electroporation device protects mice against intranasal orthopoxvirus challenge. Vaccine 2007;25:1814-23.
Fogg C, Lustig S, Whitbeck JC, Eisenberg RJ, Cohen GH, Moss B. Protective immunity to vaccinia virus induced by vaccination with multiple recombinant outer membrane proteins of intracellular and extracellular virions. J Virol 2004;78:10230-7.
Moss B. Orthopoxviruses and Their Replication. In: Knipe DM, Howley PM, editors. Fields Virology. 4th ed. Philadelphia: Lippencott, Williams and Wilkins, 2001: 1249-81.
Franke CA, Wilson EM, Hruby DE. Use of a cell-free system to identify the vaccinia virus L1R gene product as the major late myristylated virion protein M25. J Virol 1990;64:5988-96.
Ravanello MP, Hruby DE. Conditional lethal expression of the vaccinia virus L1R myristylated protein reveals a role in virion assembly. J Virol 1994;68:6401-10.
Ichihashi Y, Oie M. Neutralizing epitope on penetration protein of vaccinia virus. Virology 1996;220:491-4.
Ichihashi Y, Takahashi T, Oie M. Identification of a vaccinia virus penetration protein. Virology 1994;202:834-43.
Wolffe EJ, Vijaya S, Moss B. A myristylated membrane protein encoded by the vaccinia virus L1R open reading frame is the target of potent neutralizing monoclonal antibodies. Virology 1995;211:53-63.
Hooper JW, Schmaljohn AL, Schmaljohn C, inventors; The United States of America as represented by the Secretary of the Army, assignee. Prophylactic and Therapeutic Monoclonal Antibodies. United States of America patent 6,451,309. 2002.
Su HP, Garman SC, Allison TJ, Fogg C, Moss B, Garboczi DN. The 1.51-Angstrom structure of the orthopoxvirus L1 protein, a target of potent neutralizing antibodies. Proc Natl Acad Sci U S A 2005;102:4240-5.
Senkevich TG, White CL, Koonin EV, Moss B. Complete pathway for protein disulfide bond formation encoded by orthopoxviruses. Proc Natl Acad Sci USA 2002;99:6667-72.
Su HP, Golden JW, Gittis AG, Hooper JW, Garboczi DN. Structural basis for the binding of the neutralizing antibody, 7D11, to the orthopoxvirus L1 protein. Virology 2007; 368:331-41.
Edghill-Smith Y, Golding H, Manischewitz J, King LR, Scott D, Bray M, et al. Smallpox vaccine-induced antibodies are necessary and sufficient for protection against monkeypox virus. Nat Med 2005;11:740-7.
Panchanathan V, Chaudhri G, Karupiah G. Protective immunity against secondary orthopoxvirus infection is dependent on antibody but not on CD4 or CD8 T-cell function. J Virol 2006;80(13):6333-8.
Panchanathan V, Chaudhri G, Karupiah G. Correlates of protective immunity in orthopoxvirus infection: where does antibody stand? Immunol Cell Biol Oct. 9, 2007 (epub ahead of print).
Schmaljohn C, Vanderzanden L, Bray M, Custer D, Meyer B, Li D, et al. Naked DNA vaccines expressing the prM and E genes of Russian spring summer encephalitis virus and Central European encephalitis virus protect mice from homologous and heterologous challenge. J Virol 1997;71:9563-9.
Rodriguez JF, Paez E, Esteban M. A 14,000-Mr envelope protein of vaccinia virus is involved in cell fusion and forms covalently linked trimers. J Virol 1987;61:395-404.
Feltquate DM, Heaney S, Webster RG, Robinson HL. Different T helper cell types and antibody isotypes generated by saline and gene gun DNA immunization. J Immunol 1997;158:2278-84.
Pulford DJ, Gates A, Bridge SH, Robinson JH, Ulaeto D. Differential efficacy of vaccinia virus envelope proteins administered by DNA immunisation in protection of BALB/c mice from a lethal intranasal orthopoxvirus challenge. Vaccine 2004;22:3358-66.
Aldaz-Carroll L, Whitbeck JC, de Leon MP, Lou H, Pannell LK, Lebowitz J, et al. Physical and immunological characterization of a recombinant secreted form of the membrane protein encoded by the vaccinia virus L1R gene. Virology 2005 341:59-71.
Ashok MS, Rangarajan PN. Protective efficacy of a plasmid DNA encoding Japanese encephalitis virus envelope protein fused to tissue plasminogen activator signal sequences: studies in a murine intracerebral virus challenge model. Vaccine 2002;20:1563-70.
Rath A, Choudhury S, Batra D, Kapre SV, Rupprecht CE, Gupta SK. DNA vaccine for rabies: relevance of the trans-membrane domain of the glycoprotein in generating an antibody response. Virus Res 2005;113:143-52.
Costa SM, Paes MV, Barreto DF, Pinhao AT, Barth OM, Queiroz JL, et al. Protection against dengue type 2 virus induced in mice immunized with a DNA plasmid encoding the non-structural 1 (NS1) gene fused to the tissue plasminogen activator signal sequence. Vaccine 2006;24:195-205.
Delogu G, Li A, Repique C, Collins F, Morris SL. DNA vaccine combinations expressing either tissue plasminogen activator signal sequence fusion proteins or ubiquitin-conjugated antigens induce sustained protective immunity in a mouse model of pulmonary tuberculosis. Infect Immun 2002;70:292-302.
Li Z, Howard A, Kelley C, Delogu G, Collins F, Morris S. Immunogenicity of DNA vaccines expressing tuberculosis proteins fused to tissue plasminogen activator signal sequences. Infect Immun 1999;67:4780-6.
Wang S, Heilman D, Liu F, Giehl T, Joshi S, Huang X, et al. A DNA vaccine producing LcrV antigen in oligomers is effective in protecing mice from lethal mucosal challenge of plague. Vaccine 2004:22:3348-57.
Payne LG. Identification of the vaccinia hemagglutinin polypeptide from a cell system yielding large amounts of extracellular enveloped virus. J Virol 1979;31:147-55.
Fogg CN, Americo JL, Lustig S, Huggins JW, Smith SK, Damon I, et al. Adjuvant-enhanced antibody responses to recombinant proteins correlates with protection of mice and monkeys to orthopoxvirus challenges. Vaccine 2007;25:2787-99.
Heraud JM, Edghill-Smith Y, Ayala V, Kalisz I, Parrino J, Kalyanaraman VS, et al. Subunit recombinant vaccine protects against monkeypox. J Immunol 2006;177:2552-64.
Shinoda et al., Engineering the vaccinia virus L1 protein for increased neutralizing antibody response after DNA immunization, Virology Journal, 2009, 6:28 (http://www.vir FIGURE 5
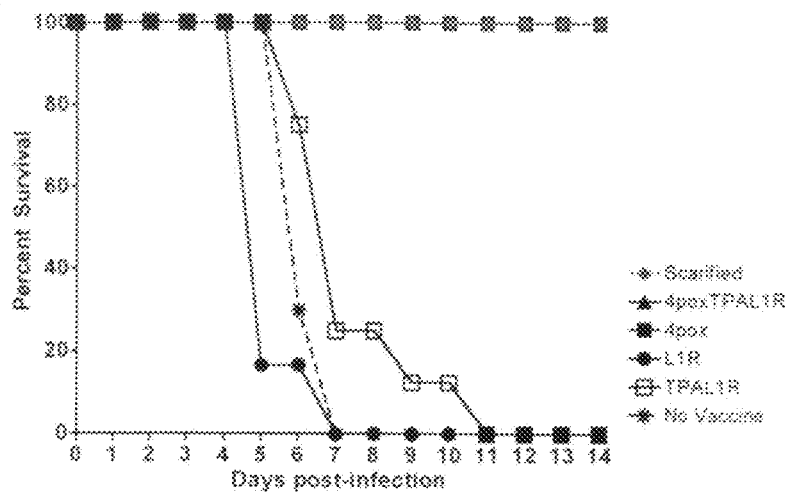
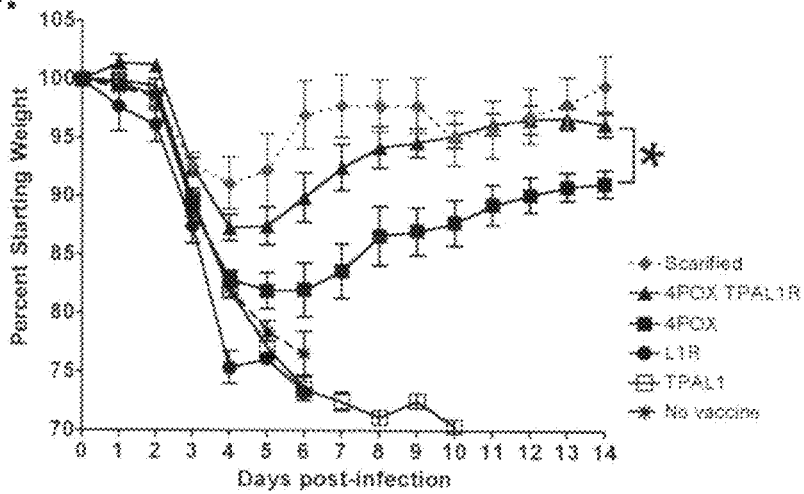

DNA IMMUNOGENIC COMPOSITION COMPRISING A FULL-LENGTH MODIFIED POXVIRUS L1R GENE FUSED TO A TPA LEADER SEQUENCE

This application claims priority from prior U.S. provisional application 60/959,927, filed Jul. 9, 2007, the entire contents of which are hereby incorporated by reference.

FIELD OF THE INVENTION

The invention described herein utilizes a modification of the L1R gene of orthopoxvirus to improve neutralizing antibody response elicited by molecular poxvirus vaccines and immunogenic compositions. The novel compositions contain full-length L1R nucleic acid and an endoplasmic reticulum-targeting sequence.

BACKGROUND OF THE INVENTION

As a consequence of a worldwide vaccination effort, smallpox as a naturally occurring disease was eradicated in the late 1970s. The threat that variola virus (VARV), the causative agent of smallpox, may be accidentally or maliciously released has led to new interest in vaccinating the military and other "first responders" against orthopoxviruses. This renewed interested in vaccination is further supported by the potential that bioinformatics coupled with synthetic biology could be used to engineer orthopoxvirus-based bioterrorism weapons. This latter threat is substantiated by recent and ongoing studies identifying the subtle genetic differences between orthopoxviruses, in particular VARV, which impact pathogenesis and viral tropism [ref. 1-3]. Additionally, naturally occurring monkeypox is an emerging zoonosis [ref. 4, 5]. Despite being localized to regions of Africa, a monkeypox outbreak recently occurred in the United States [ref. 6], representing the potential for worldwide dissemination of this orthopoxvirus.

The current licensed orthopoxvirus vaccine, Dryvax, and the newly licensed ACAM2000 consist of live vaccinia virus (VACV) [ref. 7-9]. These vaccines are highly protective and give long-lasting immunity to the vaccinated individual. However, the use of live VACV is associated with a multitude of health risks. These risks range from the potential of spreading the virus to other sites on the body, including the eye, and to non-vaccinated persons in close contact with the vaccinee [ref. 7-9]. More serious and life-threatening risks include encephalitis, progressive vaccinia, eczema vaccinatum, myocarditis, and even death [ref. 8]. Because of these health risks, vaccination is contraindicated in pregnant women, the immuno-compromised, and in persons with dermatological abnormalities, such as eczema [ref. 7-9]. Kretzschmar, M., et al recently reported that the frequency of death associated with vaccination might be higher than previously believed [ref. 10]. To diminish these heath risks, attenuated VACV viruses, such as modified vaccinia Ankara and LC8 m16 have been developed [ref. 11-14]. However, these attenuated viruses fail to induce protective immunity in immuno-compromised animals, possibly due to host defects in B-cell antibody class switching [ref. 15]. Furthermore, attenuated viruses still encode a multitude of proteins, many of which are involved in immune modulation or have unknown functions. The potential risk of these factors remains largely unexamined.

As an alternative to live virus vaccines, DNA and/or protein-based-subunit vaccines targeting one or more orthopoxvirus immunogens are being explored. Early studies demonstrated that protein or DNA-expressing A33 or B5 could protect mice from VACV challenge [ref. 16]. Recently, it was reported that vaccination with the A33 protein protects mice from challenge with ectromelia virus [ref. 17]. Currently, targets of orthopoxvirus subunits vaccines include D8, H3, A33, A27, L1 and B5 [ref. 16-24]. We developed a combination DNA vaccine (termed 4pox) that targets four orthopoxvirus antigens (L1, A27, B5 and A33) [ref. 21-23]. Orthopoxvirus has two antigenically distinct infectious forms, extracellular enveloped virions (EEV) and intracellular mature virions (IMV) [ref. 25]. EEV particles are primary involved in viral dissemination within an infected host, while the more environmentally stable IMV are thought to be involved in spread between hosts. Accordingly, our 4pox vaccine targets multiple proteins on both infectious forms of orthopoxviruses, the IMV (L1 and A27) and the EEV (B5 and A33). Plasmids expressing these genes elicit antibody responses against each protein when delivered to the skin by gene-gun or electroporation [ref. 20-23]. Importantly, the 4pox vaccine can protect mice and non-human primates from lethal challenge with VACV or monkeypox virus, respectively [ref 21-23]. Fogg, C., et al. demonstrated that a protein vaccine consisting of these targets can also protect animals from lethal orthopoxvirus challenges [ref. 24]. Thus, these combinations of orthopoxvirus targets are effective and valuable targets for a subunit orthopoxvirus vaccine.

The L1 protein is encoded by the L1R gene and is a target of the 4pox vaccine [ref. 21-23]. L1 is a myristylated 23-29 kDa membrane protein located on the surface of IMVs and beneath the envelope on EEVs [ref. 26, 27]. This molecule is highly conserved among the orthopoxviruses. Importantly, the L1 protein is a target of potently neutralizing antibodies [ref. 20-23, 28-31], making it an attractive target for vaccines and therapeutics. By "neutralizing antibody" it is meant an antibody (or antibody fragment such as an F(Ab')2 fragment) that has a mechanism of action of specifically interacting with and binding to a viral target molecule (e.g. L1) and this interaction prevents the virus from being able to productively infect a target cell by means such as (but not limited to), preventing receptor binding, preventing important conformational changes in a virus molecule (directly or indirectly) required to infect a target cell or by preventing an important cellular signaling event needed for infection.

The precise function(s) of L1 remains to be characterized because deletion is a lethal [ref. 27]. However, in the absence of L1, particle morphogenesis and formation of infectious virus is blocked, suggesting a role for L1 in IMV assembly [ref. 27]. Antibodies against L1 can neutralize viral infectivity, suggesting that L1 may also play a role in particle entry either directly or indirectly [ref. 30]. The structure of L1 has been solved and reveals a molecule comprised of a bundle of α-helices packed against a pair of two-stranded β-sheets, held together by four loops [ref. 32]. The structure also contains three disulfide bonds that are formed in the cytoplasm by a virus-encoded disulfide bond formation pathway [ref. 33]. These disulfide bonds are critical for the interaction of potently neutralizing antibodies [ref. 30]. Indeed, the crystal structure of L1 bound by a potently neutralizing antibody MAb-7D11 was recently reported [ref. 34]. This structure revealed that potentially neutralizing antibodies bind to a discontinuous epitope consisting of two loop regions held together by a disulfide bond.

It remains a problem that the current live-orthopoxvirus vaccine is associated with minor to serious adverse affects, and is contraindicated for use in a significant portion of the population. As an alternative vaccine, we have previously shown that a DNA subunit vaccine (4pox) based on four orthopoxvirus immunogens (L1R, B5R, A27L and A33R) can produce protective immunity against lethal orthopoxvirus challenges in mice and nonhuman primates. [Refs. 21 and 22] Because antibodies are critical for protection against secondary orthopoxvirus infections [ref. 35-37], we were interested in strategies that will enhance the humoral immune response against vaccine targets. To that end, we were interested in enhancing the 4pox DNA vaccine such that it will require only one or two vaccinations to elicit protection in the vaccinated host.

Another problem was encountered when we attempted to reduce the number of cartridges by co-delivery of two antigens (L1 and A33) conjugated on the same carrier particle for gene gun DNA vaccination. For multi-pox DNA vaccination, it is desirable to reduce the number of cartridges required for each vaccination, so that the capacity to deliver two or more antigens in one cartridge would be ideal. However, we discovered that when we mixed plasmids expressing L1R and A33R (e.g., precipitated on the same gold particle for gene gun delivery), there was a good response against A33 protein but essentially no response to the L1 protein (no neutralizing antibody). This is believed to be due to interference of the L1 and A33 with each other. [ref. 20]

SUMMARY OF THE INVENTION

Previously, we reported the generation of a modified full-length L1R construct where a tissue plasminogen leader sequence (tPA) was placed on the 5' end of the full-length L1R gene [ref. 23]. We found that this modified construct (pWRG/tPA-L1R) leads to the surface expression of the L1 protein, allowing for an in vitro flow cytometry-based assay to detect anti-L1 antibodies in vaccinated animals. We observed a marked increase in amount of L1 able to interact with conformation-dependent monoclonal antibodies, indicating proteins expressed from the tPA-L1R gene are folded more natively [ref. 23]. Thus, the tPA-L1R plasmid was useful for diagnostic purposes.

In developing the subject invention, we tested the immunogenicity of unmodified and modified L1R DNA vaccines, pWRG/L1R and pWRG/tPA-L1R, in mice vaccinated by gene-gun. The tPA-L1R construct produced a more robust neutralizing antibody response in vaccinated mice when the DNA vaccine was administered by gene-gun as a prime/single boost. We also found that tPA-L1R produced a higher amount of neutralizing antibodies and provided superior protection in vaccinated mice than unmodified L1R when it was combined with the other 4pox immunogens. We also found that the 4pox DNA vaccine completely protected mice from lethal challenge with VACV when given as a prime and single boost and this protection was improved by substituting unmodified L1R with the tPA-L1R immunogen.

When the tPA-L1R construct was substituted for the unmodified L1R gene in the 4pox vaccine, given as a prime and single boost, animals were better protected from lethal challenge with VACV. We discovered that adding a tPA-leader sequence can enhance the immunogenicity of the L1R gene when given as a DNA vaccine. Furthermore, our results demonstrate that a DNA-based vaccine is capable of establishing protection from lethal orthopoxvirus challenges when administered as a prime and single boost without requiring adjuvant.

This invention entails the use of the full-length orthopoxvirus L1R gene, critically including the carboxy terminus and the transmembrane region, recombinantly combined with an endoplasmic reticulum-targeting signal (such as the tPA sequence, Calreticulin, IgKappa-chain leader sequence, or any signal sequence that targets the L1 protein into the endoplasmic reticulum), as a vaccine or immunogenic composition. In its basic embodiment, the invention contemplates improved methods for generating antibodies to L1 in mammals, due to the combination of advantages attributable to the combination of the full-length L1R plus endoplasmic reticulum-targeting signal—including better binding of the antibody to the loop regions of L1 held together by a cysteine bond between Cysteine 34 and Cys 57, as described for instance in Ref. 34 (which defines the epitope as a region of L1). As is well known, this region may vary slightly for each antibody, but will always require the loop regions held by the cysteine bond. Other advantages of our methods include concentration of the L1 protein at the cell membrane and surface with reduced release of L1 from the transfected cell, proper folding of the L1 protein, and other features described here.

The L1 molecule is an ideal target for pan-orthopoxvirus subunit vaccines and therapeutics because it is a target of potently neutralizing antibodies [ref. 20, 21, 23, 28-30, 42], it is absolutely essential for replication [ref. 27], and the protective epitope is conserved between orthopoxviruses. Because L1 produced in transfected cells does not have access to an essential virus-encoded disulfide bond formation pathway, much of the protein likely folds incorrectly. By targeting the recombinant L1 to the endoplasmic reticulum (ER), it was possible to generate L1 that was folded more natively as indicated by interaction with conformationally dependent, neutralizing monoclonal antibodies. As shown below, the tPA-L1R construct was capable of enhancing neutralizing antibody responses in mice vaccinated by gene-gun. When the modified L1R construct was used in the 4pox vaccine, we observed increased protection of vaccinated animals after a prime and single boost. This was also attributed to the improved binding of the antibody to the epitope, which is due to the presence of the L1 transmembrane region. This was also attributed to the improved binding of the antibody to the epitope, which is due to the more authentic protein folding of the L1 protein due to usurpation of the endogenous disulfide bond formation machinery in the ER. The presence of the L1 transmembrane region further enhanced proper folding such that this construct (tPA-L1R), or any full-length ER-targeted L1R variant will interact efficiently with neutralizing antibodies that bind the loop regions of L1R held together by the disulfide bond between Cys34 and Cys57.

In addition to using tPA-L1R as a component in our DNA vaccine, this construct may be used to generate neutralizing antibodies in systems for producing molecules suitable for use in humans. These molecules could then be used as therapeutics or postexposure prophylactics to treat orthopoxvirus infections and/or adverse effects related to vaccination with live-virus.

The tPA-L1R construct is made as described in the Hooper et al. "Smallpox DNA vaccine delivered by novel skin electroporation device protects mice against intranasal orthopoxvirus challenge." Vaccine 2007; 25:1814-23. [ref. 23] Of particular importance is that the constructs used in the vaccines, compositions and methods of this invention include (1) the full-length L1 protein, (2) which includes the transmembrane region that significantly improves epitope binding and also causes the L1 product to be concentrated at the cell membrane with less secretion through the membrane than would occur if the L1 transmembrane region was removed, and (3) an endoplasmic reticulum-targeting signal (such as tPA, Calreticulin, IgKappa-chain leader sequence secretion signal, and any other sequence that targets L1R expression in the endoplasmic reticulum) so that the L1 protein is produced in the endoplasmic reticulum, thereby allowing the L1 protein to be properly folded.

While we knew from Reference 23 that the tPA-L1R construct was useful as a diagnostic to detect L1-specific antibodies, we were surprised at the extent to which it is immunogenic, as well as by its compatibility with and enhancement of the A33R plasmid in a combined vaccine/immunogenic composition. As shown by the data below, use of the tPA-L1R construct as a DNA-vaccine led to enhanced neutralizing antibody responses against the L1 protein in mice vaccinated by gene-gun. The neutralizing antibody responses in vaccinated mice were significantly higher than those determined in our previous studies, where mice vaccinated with L1R DNA had geometric mean titers of 235 and 101 after three vaccinations [ref. 20, 21]. By adding the tPA leader sequence to L1R, we were able to generate neutralizing antibody responses with a GMT titer of 489. Surprisingly, this high neutralization response was elicited after only two vaccinations. In the previous work, we achieved GMT titers of only 101 and 235 after three vaccinations. In addition, in the 4pox combination vaccine (tPA-L1R, B5R, A27L and A33R) we obtained GMT neutralization titers of 538 compared to 56 for the combination vaccine using the unmodified L1R.

To summarize the advantages and unexpected benefits of our invention as detailed below:

We have achieved a new DNA vaccine and immunogenic composition useful against poxviruses, using a nucleic acid encoding the full-length poxvirus L1R gene modified so that an endoplasmic reticulum-targeting signal sequence is inserted on the 5' end (hereafter referred to as "the modified L1R"). We discovered that our modified L1R plasmid had enhanced neutralizing antibody response against L1, compared with unmodified L1R. This was especially true after two vaccinations in mice, and the difference in titer levels was significant.

We have achieved a new DNA vaccine for poxviruses, using our modified L1R, combined with the nucleic acid encoding at least one (and preferably both) of the extracellular enveloped virions (EEV) of infectious orthopoxviruses (e.g., A33R and B5R), and also preferably a nucleic acid encoding another poxvirus intracellular mature virion (IMV) besides L1R (e.g., A27L). We discovered that the tPA-L1R was effective for enhancing a multi-gene DNA vaccine, by enhancing the humoral immune response, by producing a significantly higher amount of neutralizing antibodies, and by providing superior protection in vaccinated mice than unmodified L1R when it was combined with other poxvirus immunogens. Overall, substituting the tPA-L1R for the unmodified L1R in a multi-gene vaccine provided statistically greater protection from challenge, across the board.

When our new DNA vaccine was tested in mice, it completely protected the mice from lethal challenge of vaccinia virus when given as a prime and single boost. Thus, only two vaccinations were needed, which is significant because in the past a DNA vaccine targeting both IMV and EEV required three or four vaccinations to elicit protection.

Our new DNA vaccine was effective even without an adjuvant, which is significant because other studies have found that the A33 and L1 protein required addition of adjuvant when delivered as a protein vaccine (Ref. 50). It was unknown if certain IMV and EEV antigens (L1R and A33R) could elicit a protective antibody response when delivered as a gene-based vaccine after only two vaccinations in the absence of adjuvant. Of course, adjuvants may be useful, especially in the situation where our DNA vaccine or immunogenic composition includes a plasmid encoding a protein that acts as an adjuvant or are fused with an adjuvant such that the fusion generates a chimeric protein consisting of the DNA vaccine immunogen and an adjuvant molecule. Of course, for vaccines who are immunocompromised or elderly, or anyone whose immune system is not sufficiently responsive, an adjuvant may be needed.

We were concerned that targeting the L1 production to the endoplasmic reticulum would affect the type of immune response elicited against the L1, particularly the production of IgG1 antibodies. However, the presence of the tPA-L1R did not impact the IgG isotype against L1.

Typically for DNA vaccine immunogens, the transmembrane (TM) regions of the antigen are removed to allow secretion. We purposely retained the TM region to inhibit secretion and concentrate the L1 proteins at the cell surface. We also found quite unexpectedly that a secreted L1 containing only the ectodomain region did not interact with potently neutralizing antibodies as well as our full-length L1. Thus, the presence of the TM resulted in greater immunogenicity.

We had expected that adding the tPA sequence to all of the 4pox vaccine targets (A33R, L1R, A27L and B5R) would enhance neutralizing antibody production for each. However, we discovered this was not true—the tPA leader sequence was ineffective to benefit the A27L antigen when delivered using a gene gun, and in fact actually decreased its effectiveness to raise antibodies. Thus, we learned that the ability of the tPA leader sequence to enhance neutralizing antibody production appears to be antigen specific.

Also, what was quite unexpected was that that our plasmid containing the full-length L1R/endoplasmic reticulum-targeting signal was quite useful when combined with the A33R plasmid on the same carrier. In fact, this L1R plasmid can be readily mixed with the A33R plasmid and conjugated to the same carrier particle (e.g., a gold particle) for used in DNA vaccination gene-gun, with none of the problems previously encountered with the L1R plasmid that does not contain the endoplasmic reticulum-targeting signal. As shown below, we achieved acceptable expression of both the L1 and A33 proteins, and the L1 response was even enhanced as a result.

In one embodiment, our invention encompasses DNA vaccines against poxviruses, and immunogenic compositions. The DNA vaccines and immunogenic compositions comprise a nucleic acid encoding the full-length poxvirus L1R gene modified so that an endoplasmic reticulum-targeting sequence (such as, for example, tissue plasminogen leader sequence (tPA), Calreticulin, IgKappa-chain leader secretion signal, and any other endoplasmic reticulum-targeting sequence) is inserted or otherwise operably linked on the 5' end. By "L1R gene" it is meant the known sequence of wild-type L1R, or its optimized codon sequence, or any full-length L1 ortholog that may be properly folded, contains a transmembrane region, and contains the neutralizing epitopes recognized by the known potent monoclonal antibodies MAb-10F5 and/or MAb-7D11. By "codon optimized" is it meant that the L1R gene was altered such that the nucleic acids were changed to those that allow the use of non-limiting tRNA pools from mammalian cells; and also the gene was altered at the nucleic acid level so that its mRNA is made more stable and thereby expresses protein longer. The nucleic acid sequence was changed without altering the coded amino acid sequence. This was accomplished by codon optimizing the tPAL1R. The process of codon optimization not only changed the nucleic sequence, but also it was intended to allow more efficient codon usage and increased stability of the mRNA produced by the plasmid. An algorithm called GeneOptimizer (patent pending), owned by GeneArt was used to allow more efficient codon usage and stabilization of the mRNA.

We found that both the codon optimized version and the non-codon optimized tPA-L1R were effective in raising potent neutralizing antibodies. However, the codon optimized version showed enhanced protection in a side-by-side comparison—i.e. more animals survived being vaccinated by tPA-L1R codon optimized than tPA-L1R that was not codon optimized.

The DNA vaccines are preferably present in amounts sufficient to induce a protective immune response in a mammal, including a human, cattle, and any other animal susceptible to infection by an orthopoxvirus and that would be benefited by intervention to prevent such an infection by use of a vaccine or an immunotherapeutic generated by use of the tPA-L1R construct.

The immunogenic compositions are preferably present in an amount to elicit an immune response in an animal susceptible to a poxvirus, or in an amount sufficient to generate neutralizing antibodies specific for the L1R antigen, or in an immunogenically effective amount. The DNA vaccine and immunogenic composition are preferably given in at least two doses, although one dose may be sufficient in certain circumstances (e.g., when given in conjunction with another immunogenically effective component or antigen, or when used to boost a person or animal previously vaccinated with the live-virus orthopoxvirus vaccine (such as ACAM2000), or as a priming vaccine whereby the person or animal will be vaccinated with the DNA vaccine describe here, and then subsequently boosted with live-virus vaccine (e.g., ACAM2000) or similar (MVA) for the intended purpose of focusing the immune responses against the L1, and A33 or B5 and possible A27 targets.

In a preferred DNA vaccine and immunogenic composition, the modified L1R (or its ortholog product) is combined with at least one of the EEV poxvirus nucleic acids selected from the group consisting of a nucleic acid encoding A33R (or its ortholog product) and a nucleic acid encoding B5R (or its ortholog product), and optionally a nucleic acid encoding poxvirus A27L (or its ortholog product). Also contemplated are the homologs and orthologs of these antigens.

Furthermore, it is preferred that the vaccines and immunogenic compositions described herein—whether DNA vaccine or protein vaccine/immunogenic composition—contain redundant IMV and EEV targets since this will increase cross-reactivity and cross-protection. Having such redundancy will provide enough or more than enough cross-reactive epitopes so as to afford vaccine protection—that is, because the proteins are so similar, the redundant nature of a DNA vaccine containing two, three or four of the genes/gene products compensates for the possibility that the antibody to one protein won't cross-react with a particular virus. Hence, it is most preferred that the vaccines and immunogenic compositions contain at least two (one being the L1R as modified), preferably three, and most preferably all four of the genes/gene products L1R as modified, A27L, A33R and B5R, or the respective orthologs.

As described in detail below, the inventors have developed poxvirus vaccines and immunogenic compositions useful in connection with poxviruses including vaccinia virus, variola virus (smallpox), monkeypox virus and other orthopoxviruses, and virtually any poxvirus having 90% or more amino acid sequence identity for the L1R gene product (of course, not inclusive of the tPA portion) and 90% or more amino acid sequence identity of at least one of the A33R or B5R gene products, and preferably also 90% or more amino acid sequence identity of the A27L gene product, at the amino acid level. In particular, it is preferable that a vaccine against infection by one of these viruses, or immunogenic composition, contains in addition to the modified L1R, both of A33R and B5R, or both A33R and A27L, or both B5R and A27L, and even more preferably contains all of A33R, B5R and A27L. Preferably, the modified L1R gene is SEQ ID NO:1 (the tPA-L1R), or SEQ ID NO:3 (the codon optimized L1R).

However, due to the high homology between poxviruses, and orthopoxviruses in particular, where the poxvirus has orthologs of the L1R, A33R, A27L or B5R genes, and those orthologs produce proteins/peptides that share 90% identity with the amino acid sequence of the gene products of the L1R, A33R, A27L and/or B5R genes, those poxvirus ortholog gene products may be used as vaccine components for other poxviruses—as long as those other poxviruses themselves have orthologs that produce proteins/peptides that share 90% identity with the amino acid sequence of the gene products the L1R, A33R, A27L or B5R genes.

In this invention, the term "ortholog" denotes the well-known meaning of this term. In this art, orthologs are genes in different species which evolved from a common ancestral gene. Due to their separation following a speciation event, orthologs may diverge, but usually have similarity at the sequence and structure levels; furthermore, orthologs usually have identical functions. Orthology is a type of homology. In this application, the term ortholog is used to include the ortholog gene (DNA or RNA) or the peptide/protein product of the ortholog. Sometimes the peptide/protein product of the ortholog is referred to as "ortholog product" or simply "ortholog". The meaning is evident from the context (e.g., a protein vaccine or immunogenic composition will contain peptides or proteins that may be referred to as orthologs—that is, products of an ortholog gene—of another poxvirus; a nucleic acid vaccine will contain nucleic acids that may be referred to as orthologs of another poxvirus—that is, an ortholog gene).

The ortholog products having 90% identity are preferably derived from an orthopoxvirus selected from the group consisting of: camelpox virus, ectromelia virus, raccoon poxvirus, skunk poxvirus, Tatera poxvirus, Uasin Gishu virus, Volepox virus, variola virus, vaccinia virus, monkeypox virus, gerbilpox and cowpox virus, or any genetically modified orthopoxvirus which contains a homolog of the L1 molecule (or an engineered L1 molecule retaining sufficient homology to retain neutralizing epitopes), and optionally homologs from the other antigen targets. For instance, monkeypox and variola would be targeted by the immune response against L1 generated by our vaccines and immunogenic compositions.

Due to the high homology between poxviruses, and the known data regarding the cross-protection by vaccines derived from them, this DNA vaccine may be protective against poxviruses including orthopoxvirus such as camelpox virus, ectromelia virus, raccoon poxvirus, skunk poxvirus, Tatera poxvirus, Uasin Gishu virus, Volepox virus, variola virus, vaccinia virus, monkeypox virus, gerbilpox and cowpox virus, or genetically engineered versions thereof. The proteins of interest are those ortholog products that correspond to the products of the L1R modified as discussed above, A33R, A27L, and/or B5R genes, which have 90% identity. If the corresponding virus has, for instance, only 50% homology with variola virus, but the ortholog products of at least two of the gene products of L1R, A33R, A27L, and B5R have at least 90% identity in the amino acid sequence, then these ortholog products are useful as a vaccine for that virus. For instance, the camelpox virus has ortholog products that have at least 90% identity with the gene products of L1R, A33R, A27L, and B5R, and those ortholog products (two or more) will be useful as vaccine components of a vaccine against camelpox. The key is that the ortholog products have at least 90% identity to the gene products of L1R, A33R, A27L, and B5R.

In the context of all embodiments of this invention as described herein, these vaccines and immunogenic compositions are based on recombinant DNA, proteins or peptides that, when administered to a person or mammal, confer protection from poxviruses. (By "peptides" it is meant an amino acid sequence that is less than the full-length protein sequence.)

Thus, what is described here, in one embodiment, is a gene-based or protein-based replacement or enhancement vaccine and vaccination methodology to effectively protect against variola virus (smallpox), monkeypox virus, other poxviruses having 90% amino acid identity, and engineered poxviruses without any of the drawbacks associated with live-virus vaccines. This is especially relevant to immunocompromised persons who cannot be vaccinated with live vaccinia virus. It also represents an improvement over DNA vaccines alone, in terms of being simpler and more convenient, and often more effective.

It is preferred that the vaccines are effective such that, following administration in two separate vaccinations to a mouse exposed to vaccinia virus, generates a neutralizing antibody response to the L1 protein with a GMT titer of over 400. Based on what is known in the art about vaccines, this titer level can be extrapolated to humans as well—so it is preferred that a prime and boost vaccination schedule in humans would also generate a neutralizing antibody response to the L1 protein with a GMT titer of over 400.

As noted above, our DNA vaccine needs no adjuvant, that is, is effective in the absence of an adjuvant, especially for the immunogens L1R and A33R when co-delivered. However, if an adjuvant is used, it may be any adjuvant known in the art, as would be determined by someone skilled in this art. Examples of adjuvants may be CpG, alum, immune modulatory molecules, Toll-like receptor (TLR) stimulators and co-stimulatory markers. Any known adjuvant that does not interfere with the efficacy or safety of the vaccine may be used.

In another embodiment, our invention contemplates methods for inducing in a mammal an immune response against poxvirus infection. The method comprises administering to a mammal (including a human) who would be susceptible to infection by a poxvirus an immunologically effective amount of a composition comprising our modified L1R as described above (in any of its variations including its ortholog, either codon optimized or non codon optimized). The modified L1R is not likely to be a protective vaccine in the absence of at least one other infectious particle type IMV or EEV (and preferably EEV). However, our modified L1R is shown by our data to elicit high amounts of neutralizing antibody by itself, and consequently is useful by itself as an immunogenic composition that can induce an immune response in a mammal. Such an immunogenic composition has utility as, for instance, an immunotherapeutic.

In a preferred embodiment to raise a protective immune response, the composition comprises the modified L1R and at least one of the poxvirus EEV nucleic acids selected from the group consisting of a nucleic acid encoding A33R (or its ortholog) and a nucleic acid encoding B5R (or its ortholog), and optionally (and preferably) the IMV nucleic acid encoding poxvirus A27L (or its ortholog). Preferably, the composition comprises both of the EEV nucleic acids, and more preferably all of A33R, B5R and A27L, or the respective orthologs. Preferably the endoplasmic reticulum-targeting sequence is tPA, Calreticulin or IgKappa-chain leader sequence. Preferably, the modified L1R is SEQ ID NO:1 or SEQ ID NO:3 (codon optimized).

The poxvirus protected against may be an Orthopoxvirus chosen from the group consisting of: camelpox virus, ectromelia virus, raccoon poxvirus, skunk poxvirus, Tatera poxvirus, Uasin Gishu virus, Volepox virus, variola virus, vaccinia virus, monkeypox virus, and cowpox virus, or any genetically modified orthopoxvirus which contains a homolog of the L1 molecule (or an engineered L1 molecule retaining sufficient homology to retain neutralizing epitopes), and optionally homologs from the other antigen targets.

In this method the DNA vaccine may be administered as a single dose, although it is preferably administered first as a prime vaccine and again subsequently as a booster vaccine. A third, fourth, or more, vaccination may be desirable in situations where a vaccinee's immune responses against the vaccine has to be boosted, for example, yearly boosting to maintain a high titer, or in the immunocompromised vaccinee where more vaccinations are needed to boost immunity. For instance, a single dose vaccine protocol may comprise the step of administering to a human or other mammalian subject an immunologically effective amount of one of the DNA vaccines described herein.

For a preferred prime-boost regimen such a vaccine protocol may comprise the steps of (a) administering to a human or other mammalian subject an immunologically effective amount of one of the DNA vaccines described herein; and (b) subsequently administering to the subject an immunologically effective amount of the DNA vaccine. As discussed below, we were surprised that only two vaccinations were necessary to completely protect the mammals.

As noted herein, these DNA vaccines are surprisingly effective in the absence of an adjuvant, especially when the prime-boost schedule is used. However, if desired an adjuvant may be included. Any adjuvant that does not inhibit the vaccine activity or safety would be acceptable, including those adjuvants described herein.

Administration of DNA vaccines is described in U.S. Pat. No. 6,562,376. The DNA vaccine may be administered to the subject by intramuscular injection, intradermal injection, gene gun, electroporation, or biojector. For instance, see Hooper et al., Journal of Virology, Vol. 82, No. 3, February 2008, pages 1332-1338 (published ahead of print on Nov. 21, 2007), which describes the general use of electroporation administration of DNA vaccines such as ours. Other methods include viral-based gene delivery vector, such as Venezuelan Equine Encephalitis (VEE) replicons, adenovirus, and the like, either live or replication incompetent. For instance, see Mathias Liniger, Armando Zuniga, Hussien Y Naim. Use of viral vectors for the development of vaccines. Expert Rev. Vaccines 6:255-266 (2007), which describes the general use of viral vectors for use with vaccines such as ours. Any mechanism that elicits a potent response is acceptable. Generally speaking, the preferred modes of administration are by gene gun and electroporation. For instance, one method of administration using a gene gun comprises the steps of (i) coating the nucleic acids onto carrier particles, which nucleic acid sequences are each operatively linked to a promoter operative in cells of a mammal; an (ii) accelerating the coated carrier particles into epidermal cells of the mammal in vivo. The nucleic acids may be conjugated on carrier particles and the carrier particles are administered to the mammal by accelerating them into the epidermal cells of the mammal. The carrier particles may be any known in the art, for instance gold particles, silver particles, platinum particles, tungsten particles, polystyrene particles, polypropylene particles, and polycarbonate particles.

In another preferred embodiment using a gene gun or the equivalent, the DNA vaccine comprises at least one carrier particle, having coated thereon (1) a DNA sequence comprising a promoter operative in the cells of a mammal and operatively linked to the modified L1R (in any of its variations or ortholog) and (2) a DNA sequence comprising a promoter operative in the cells of a mammal and operatively linked to a protein coding region encoding the A33R antigen or its ortholog. This is significant because heretofore it was not feasible to have L1R and A33R co-delivered on the same carrier particle. It is also preferred that the B5R and/or the A27L antigens, or their orthologs, be coated onto the same particle as the modified L1R-A33R antigens. In this way, all or as many as is desired are co-delivered on the same carrier particle. Alternatively, the B5R and/or A27L may be coated onto separate particles if desired, and delivered alongside the particles containing the modified L1R-A33R antigens.

In another preferred variation, the DNA vaccine can comprise at least two carrier particles. One of the carrier particles may be the modified L1R/A33R combination as just described, or just the modified L1R operably linked to a promoter operative in the cells of a mammal may be on carrier particle without A33R. The second or additional carrier particle has a DNA sequence coated thereon, the DNA sequence comprising a promoter operative in the cells of a mammal operably linked to a protein coding region encoding for a poxvirus antigen chosen from the group consisting of: A33R antigen, A27L antigen, B5R antigen, a ortholog of A33R antigen, a ortholog of A27L antigen, and a ortholog of B5R antigen, wherein the at least two carrier particles each have a DNA sequence coated thereon having a protein coding region encoding for a different poxvirus antigens. Preferably the second particle will be one of the EEV antigens or its ortholog. Such a DNA vaccine composition, for administration by a gene gun or similar device, is described in U.S. Pat. No. 6,562,376.

Because of the known cross-protection between the various poxviruses, the protein products of the L1R, A33R, A27L and B5R genes from virtually any orthopoxvirus may be effective in this vaccine method. It is known that there are high levels of similarity between variola virus and other orthopoxviruses. Esposito et al., Science, Vol. 313, Aug. 11, 2006, pages 807-812. It is also known that vaccinia orthologs elicit protective immunity against monkeypox. In the field of poxviruses, orthologs have very high homology and functionality. Thus, orthologs of the protein products of the VACV L1R, A33R, A27L and B5R genes would be useful in the protein vaccine component of this method, especially orthologs having 90% identity with the protein products of these VACV genes. Such orthologs having 90% identity are preferably derived from an orthopoxvirus selected from the group consisting of: camelpox virus, ectromelia virus, raccoon poxvirus, skunk poxvirus, Tatera poxvirus, Uasin Gishu virus, Volepox virus, variola virus, vaccinia virus, monkeypox virus, gerbilpox and cowpox virus, or genetically engineered versions thereof. To that end, it is known that many of these orthopoxviruses share more than 90% identity in the orthologs of the four genes of interest (e.g., variola, monkeypox, vaccine, camelpox, mousepox (ectromelia)). For the purposes of this invention, if the corresponding virus has, for instance, only 50% homology with vaccinia virus, but the orthologs of at least two of the gene products of L1R, A33R, A27L and B5R have at least 90% identity in the amino acid sequence, then these orthologs are useful as a vaccine for that corresponding virus.

For instance, the variola virus has ortholog genes to the VACV genes L1R, A33R, A27L, and B5R. Further, the variola ortholog gene products have at least 90% identity with the gene products of L1R, A33R, A27L, and B5R. Those variola ortholog products will be useful as vaccine components of a vaccine against variola. Correspondingly, and very important to this embodiment of the invention, the vaccinia gene products of L1R, A33R, A27L, and B5R genes will also be useful as a vaccine against variola, and the variola ortholog products will be useful as a vaccine against vaccinia. The key is that the ortholog products have at least 90% identity to the gene products of L1R, A33R, A27L, and B5R. It is noted here that the monkeypox ortholog genes M1R, A35R, A29L, and B6R produce peptides/proteins that also have at least 90% identity with the gene products of L1R, A33R, A27L, and B5R, and consequently would be useful as vaccine components in a vaccine against vaccinia or variola.

Regarding monkeypox, for instance, which has the M1R as the equivalent of L1R, the modified L1R and the vaccines containing it would protect against infection due to high homology. In addition, our vaccine could be made such that we used the immunogens—modified L1R, A33R, B5R, and A27L orthologs—from another orthopoxvirus, i.e. using the variola genes as the vaccine and not the vaccinia genes.

In another embodiment, our invention entails a composition of matter comprising a nucleic acid encoding the modified L1R gene (as described above in all variations and orthologs), and at least one of the poxvirus nucleic acids selected from the group consisting of a nucleic acid encoding A33R, a nucleic acid encoding B5R, and a nucleic acid encoding poxvirus A27L. Such a composition of matter may be useful for generating high titer poxvirus neutralizing antibodies for diagnostic, therapeutic and prophylactic use. As shown below, data shows the successful use of the pWRG/tPA-L1R construct to generate high titer neutralizing antibodies in rabbits using muscle electroporation. This is an improvement over the known pWRG/L1R construct which worked poorly when we tried to elicit neutralizing antibodies in rabbits by electroporation.

To that end, our invention also contemplates methods for generating neutralizing antibodies in humans and other mammals, comprising the steps of
(a) administering (preferably by muscle electroporation) to a mammal or avian species (such as a human, rabbit, duck or any genetically modified animals that produce human antibodies) the modified L1R gene, under conditions that the L1R will express full-length, correctly folded L1 protein in the endoplasmic reticulum of cells of the mammal, in an amount of L1 protein so as to generate high titer (such as for instance, preferably a GMT of 400 or even greater) or potent neutralizing antibodies, and
(b) collecting the neutralizing antibodies by conventional methods known in the art (e.g., the antibodies may be collected in a suitable way to maintain efficacy and for use as a safe therapeutic, including, but not limited to IgG purification by protein A or G, or other known means of antibody purification, such as affinity purification).

In another embodiment, our invention entails a DNA cassette that is capable of being cloned into other gene-based molecular vaccine delivery systems such as alphavirus replicons (such as VEE), and adenovirus replicons. The DNA cassette comprises (1) the modified L1R described above (in any of its variations and orthologs) (2) linked to a promoter or an internal ribosome entry site operable in a eukaryotic expression system, and (3) operably linked to a start codon, at least one stop codon and a poly adenylation (polyA) sequence. As is well known, the polyA sequence is critical for efficient expression, and is placed on the 3' end of the gene, after the stop codon.

BRIEF DESCRIPTION OF THE FIGURES

FIG. 5. VACV challenge of vaccinated mice. Groups of mice vaccinated twice by gene-gun with the indicated DNA vaccine or once by tail scarification with live VACV were challenged with $2\times10^6$ pfu of VACV strain IHD-J. Mice were weighed daily for 14 days. A) Survival curves for each group are shown. 100% of the mice in the scarified, 4pox(tPA-L1R), and 4pox survived. B) The percent weights of surviving mice were calculated relative to starting weights (day 0) and plotted. The differences in weight loss between the 4pox and 4pox(tPA-L1R) groups were significant for every time point starting on day 3 (p<0.05) as denoted by the asterisk.

We were able to express L1R containing a IgG kappa secretion signal. We examined if the enhanced expression of L1 when tPA was added was specific to the tPA leader signal or if other secretion signals could also lead to L1R expression. To this end, the L1R gene was cloned in frame with an IgG kappa secretion signal (on the pDisplay vector). COS cells were then transfected with pWRG/TPA-L1R or pDisplay/L1R and surface expression of L1R analyzed by flow cytometry. As shown, addition of an IgG kappa leader sequence does lead to the expression of L1 in transfected cells. Thus, in addition to tPA, another secretion signal can also lead to L1 expression.

Figure 10:
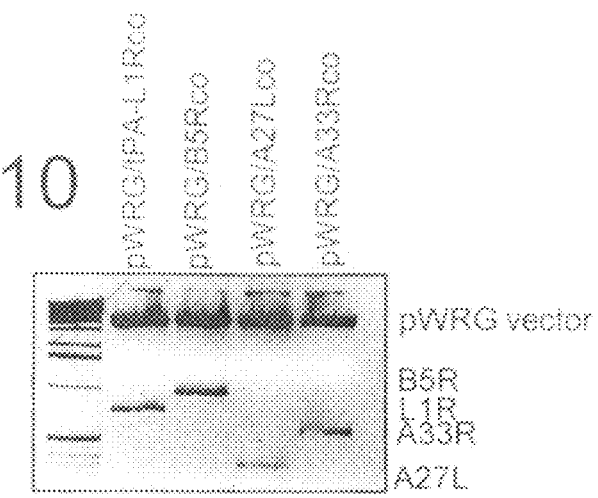
Figure 11:
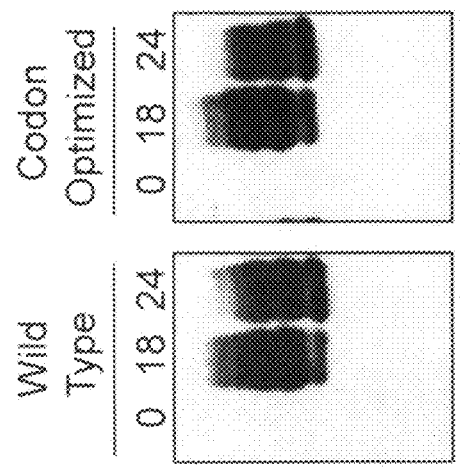
Figure 12:
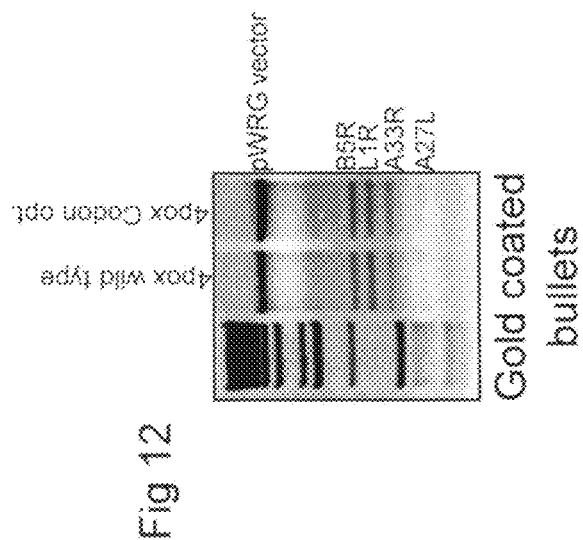

FIG. 10. Cloning codon optimized genes into the pWRG vector. Codon optimized genes (Gene Art) were PCR amplified with gene-specific primers. PCR products were digested with Nhe I and BglII (L1R) or NotI and BglII (A33R, A27L and B5R) and cloned into pWRG/TPA (L1R) or pWRG (A33R, A27L, B5R). pWRG/TPA contains a tissue plasminogen activator signal sequence. Genes were designated pWRG/TPA-L1Rco, pWRG/A33co, pWRG/B5Rco and pWRG/A27Lco. Conclusion: Codon optimized genes have been cloned into our vaccine vector pWRG or pWRG/TPA. The following is the number of changes between the wild type poxvirus genes and the codon optimized genes.

A33—137
B5R—311
A27L—90
L1R—210

These changes represent the number of nucleotide changes made to the gene to make it codon optimized: The amino acid sequence of the molecules was not altered, just the nucleotides.

FIG. 11. Expression of codon optimized genes in 293T cells. 293T cells (4×10(6)) were transfected with wild-type gene pWRG/TPA-L1Ror the codon optimized gene, pWRG/TPA-L1Rco, using Fugene6 transfection reagent. Lysates were generated at the indicated time points using tris lysis buffer. Lysates were quantitated for protein concentrations and 20 ug total lysate was used to assess protein expression levels by Western blot. Protein concentration matched lysates were run on a 10% gel (SDS-PAGE) and transferred to nitrocellulose membrane. Membranes were blocked overnight with 5% milk in Tris buffered saline containing tween (TBT-T). Membranes were then incubated with protein anti-L1 MAB-10F5 and anti-mouse secondary antibody conjugated to horseradish peroxidase. Bound antibody was detected by treating the nitrocellulose filters with enhanced chemilumescence detection reagents (Pierce) and exposing the filters to X-ray film. This shows the number of changes between the wild type poxvirus genes and the codon optimized genes. These numbers could be placed into the text. Conclusion: tPA-L1R and codon-optimized tPA-L1R both express at similar levels.

FIG. 12. Generation of DNA-coated gold microcarriers for gene-gun vaccination. Plasmid DNA for each antigen (L1R, B5R, A33R and A27L) was precipitated onto the same ~2 uM diameter gold beads at a concentration of 1 ug DNA/1 mg gold (each gene is present at ~0.25 ug DNA/1 mg gold). This DNA-gold mixture was coated on the inner surface of irradiated Tefzel tubing and the tubing was cut into 0.5-in cartridges. Each cartridge contained ~0.25-0.5 ug of DNA coated on 0.5 mg gold. To ensure equal coating of the wild-type versus codon optimized cartridges, DNA was precipitated off two gold cartridges and digested with NheI, NotI and BglII. Digested DNA was then analyzed on a 0.8% agarose gel.

FIG. 13. High-titer neutralizing antibodies produced in rabbits vaccinated with pWRG/TPA-L1R. Rabbits were vaccinated 3 times with unmodified L1R plasmid. pWRG/L1R or modified L1R plasmid, pWRG/TPA-L1R. The anti-L1 antibody response was measured by L1-specific ELISA (limit of detection was a titer=2 log). The neutralizing antibody response was evaluated by PRNT (limit of detection was a titer of 20). Animals vaccinated with an irrelevant plasmid served as negative controls for nonspecific binding and neutralizing antibody.

FIG. 14. Enhanced survival of mice vaccinated with codon optimized tPA-L1R versus wild-type tPA-L1R. VACV challenge of DNA vaccinated mice. Groups of mice vaccinated twice by gene gun with the indicated DNA vaccine (codon optimized tPA-L1R [COD L1R] or wild-type tPA-L1R [L1R]) or once by tail scarification with live VACV were challenged with $2\times10^6$ pfu of VACV strain IHD-J. A negative control mouse was also challenged (grey dashed line). Survival of individual mice were monitored for 21 d p.i. The percent survival of each group of mice are shown.

DETAILED DESCRIPTION

By our novel vaccines and compositions, we have developed methods to significantly enhance the capacity of L1R to elicit high-titer neutralizing antibodies.

In nature, the L1 protein is produced in the cytoplasm of orthopoxvirus-infected cells. L1 contains three disulfide bonds normally formed by a virus-encoded disulfide bond formation pathway [ref. 32-33]. The requirement for disulfide bonds in the interaction of several potently neutralizing monoclonal antibodies, including MAb-7D11 and MAb-10F5, has been reported [ref. 30, 34]. However, the precise structural role of these bonds in formation of the antibody epitope(s) was not clear until recently when the structural basis for the binding of potentially neutralizing antibodies to the L1 protein was reported [ref. 34]. These data reveal a discontinuous epitope containing two loops bound by a single disulfide bond. These findings support a conclusion that in the absence of the virus-encoded disulfide bond formation pathway (such as in a transfected cell), the majority of L1 folds improperly and the critical antibody epitope is not formed. Improper folding was likely responsible for the low anti-L1 responses generated in our previous studies [ref. 20, 21]. It also provides a reason as to why other groups have been unable to generate anti-L1 responses with potent neutralizing activity when vaccinating with L1R DNA [ref. 41].

Because disulfide bonds do not readily form in the cytoplasm, the virus has a cascade of viral enzymes involved in forming the disulfide bonds. When an L1R DNA vaccine is used to transfect mammalian cells, the L1 protein is expressed in the cytoplasm but the amount of correctly folded L1 protein is sub-optimal because correct disulfide bond formation is inefficient. In this invention, we have discovered that it is advantageous to target the L1 protein to the endoplasmic reticulum where cellular enzymes involved in disulfide bond formation are located. Specifically, the orthopoxvirus L1R gene was modified to encode a tissue plasminogen activator (tPA) signal sequence at the amino-terminus. The tPA signal sequence is routinely used in the art to allow the secretion of expressed proteins because after the protein is targeted to the endoplasmic reticulum signal peptidase cleaves off the signal sequence and the protein is secreted. However, as shown below, the L1 protein produced by our construct concentrated at the cell surface, with less secretion than would be expected if the transmembrane region was removed. This ended up being a surprising benefit as described below.

Another critical aspect of our invention is that it entails the full-length L1 protein including the carboxy terminus of the protein. The carboxy terminus of the L1 protein contains transmembrane regions. By retaining these sequences, our correctly folded L1 protein is not efficiently secreted from the cell. Thus, our invention allows for the expression of high-levels of L1 correctly folded so that highly-potent neutralizing antibody epitopes are formed. Moreover, this protein remains concentrated within the cell and on the cell surface.

Our experimental findings indicate that vaccination of animals with gene-based vaccines containing our construct elicits significantly higher poxvirus neutralizing antibody levels than previously achievable with any gene-based molecular vaccine. In fact, we are able to achieve neutralizing antibody titers greater than those produced in animals hyperimmunized with live virus. This modification of the L1R gene produces more natively-folded L1R protein in transfected cells which when used as a DNA vaccine leads to the generation of antibodies against the neutralizing epitopes of the L1 protein. Currently, when used in vaccines the L1R gene is delivered without this modification and is poorly expressed in cells, and produces low antibody responses in vaccinated animals. Additionally, vaccination with purified L1 protein has been done by others, but these studies used a truncated form of L1 that lacks the transmembrane region. In these protein studies, they failed to generate potently neutralizing antibodies that target an epitope located near amino acid 35 (Vaccinia L1R gene).

This invention solves expression/folding problems of the L1 molecule, a problem that had previously hampered the development of neutralizing antibodies against the L1 protein in vaccinated animals. Furthermore, it solves problems with vaccination using a truncated form of the L1 protein, in that this current invention allows for expression of full length, natively folded L1R, which does not require purification of the protein—as vaccination can be done with the gene itself by various gene-based molecular vaccine delivery systems (gene-gun, VEE-replication, adenovirus delivery, and electroporation).

The methodology using viral replicon systems is generally known. Basically, the immunogens (tPA-L1R) are inserted into a VRP expression system which packages the immunogen, along with the necessary viral transcriptional/translation machinery into a VEE particle that is functional, but replication incompetent. This particle infects a target cell (in the vaccinee) and this result in expression of the immunogen, which in turn gets intercepted by the host immune system and an immune response ensues. The virus vector systems, like the replicon (and adenovirus), are another means of delivering our gene-based vaccine to a host, just as gene-gun or electroporation, but instead of using mechanical means of delivering the gene (electricity or gold-particle bombardment) the immunogen packaged into the virus structure carries out the delivery, capitalizing on the biology of the virus.

One of the points of novelty of this invention is a means to express high-levels of correctly folded full-length, orthopoxvirus L1 protein within transacted mammalian cells. The addition of the leader sequence that trafficks L1 protein into the endoplasmic reticulum permits the proper folding of the L1 protein in vaccinated host cells. Proper display of the L1R-neutralizing epitopes to the immune system subsequently leads to the generation of highly-potent neutralizing antibodies, which could protect the host from viral challenge (vaccinating). Previous studies (not involving L1R) have used the tPA leader signal for modification of DNA vaccine targets/antigens, but these studies sought to generate secreted protein and used molecules that lack the transmembrane regions. Our use of the tPA was for the purpose of targeting L1R to the endoplasmic reticulum/golgi, where it could take advantage of the folding machinery and become folded more natively. The novelty of this design is that typically a tPA leader is added to generate secretary protein (i.e., lacking the transmembrane region). The L1R in this design still contains transmembrane region and is retained in the cellular plasma membrane. Along those lines, we have found that a full-length (i.e., not truncated) L1 protein is required to obtain potent neutralizing antibodies.

It is believed that the capacity of the tPA leader to traffic molecules through the endoplasmic reticulum (ER) is the mechanism by which the tPA leader enhances the generation of neutralizing monoclonal antibodies in tPA-L1R vaccinated animals. Within the ER, L1 can usurp the host disulfide bond formation machinery and thereby fold correctly. Consequentially, preservation of the critical epitope would permit generation of potently neutralizing antibodies. We observed that enhanced interaction of tPA-L1 with neutralizing antibodies did not seem to be specific to the tPA signal, as adding an IgG kappa leader sequence also led to increased interaction of L1 with neutralizing antibodies in transfected COS cells (data not shown). The addition of the tPA leader sequence has been employed to enhance antibody responses against numerous antigens, including the orthopoxvirus D8L gene and the Japanese encephalitis virus envelope protein [ref. 19, 43].

Figure 1:
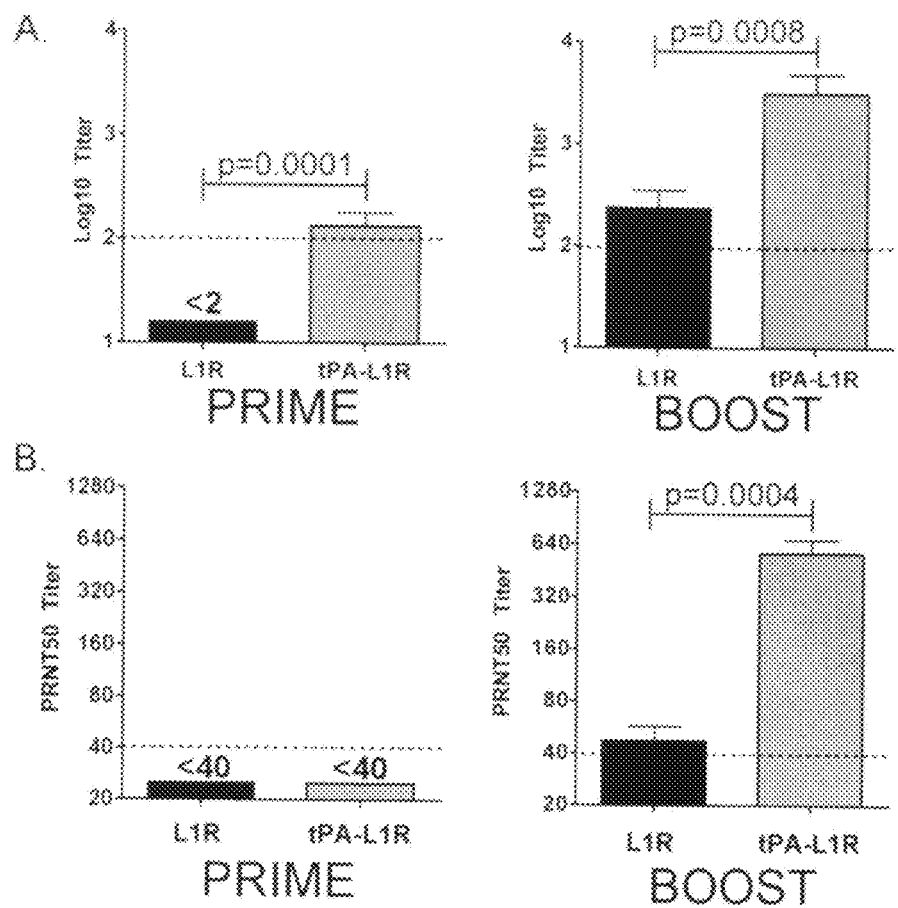
FIG. 1. Antibody responses against L1 in L1R- and tPA-L1R-vaccinated mice.
A) Purified L1 was plated in the wells of a 96-well plate (300 ng/well) in carbonate buffer. Serum from mice vaccinated (prime or boost as indicated) with either L1R or tPA-L1R DNA was serially diluted tenfold (from 1:100) and incubated with purified protein. Plates were then incubated with a secondary anti-mouse antibody (1:1000) conjugated to HRP. ABTS was added to each well and reactions were terminated using 5% SDS. Endpoint titers were calculated as described in the materials and methods. Data were plotted as a mean titer for each group +/−standard deviation. B) Serum from L1R or tPA-L1R vaccinated animals (prime or boost as indicated) was serially diluted twofold and incubated with ~50 pfu of VACV strain IHD-J for 1 h at 37° C. Antibody-virus mixtures were adsorbed to confluent monolayers of BSC-1 cells for 1 h at 37° C. After adsorption, a 1:1 mixture or 2×EBME and 3% methyl cellulose was added to each well. Three days postinfection, plaques were visualized by staining monolayers with 1.5% crystal violet. 50% neutralization titers were calculated relative to the plaque count for virus that was not incubated with serum. Data were plotted as a mean titer for each group +/−standard deviation. The lowest dilution tested was 1:40 (dashed-line indicates limit of detection).
Figure 2:
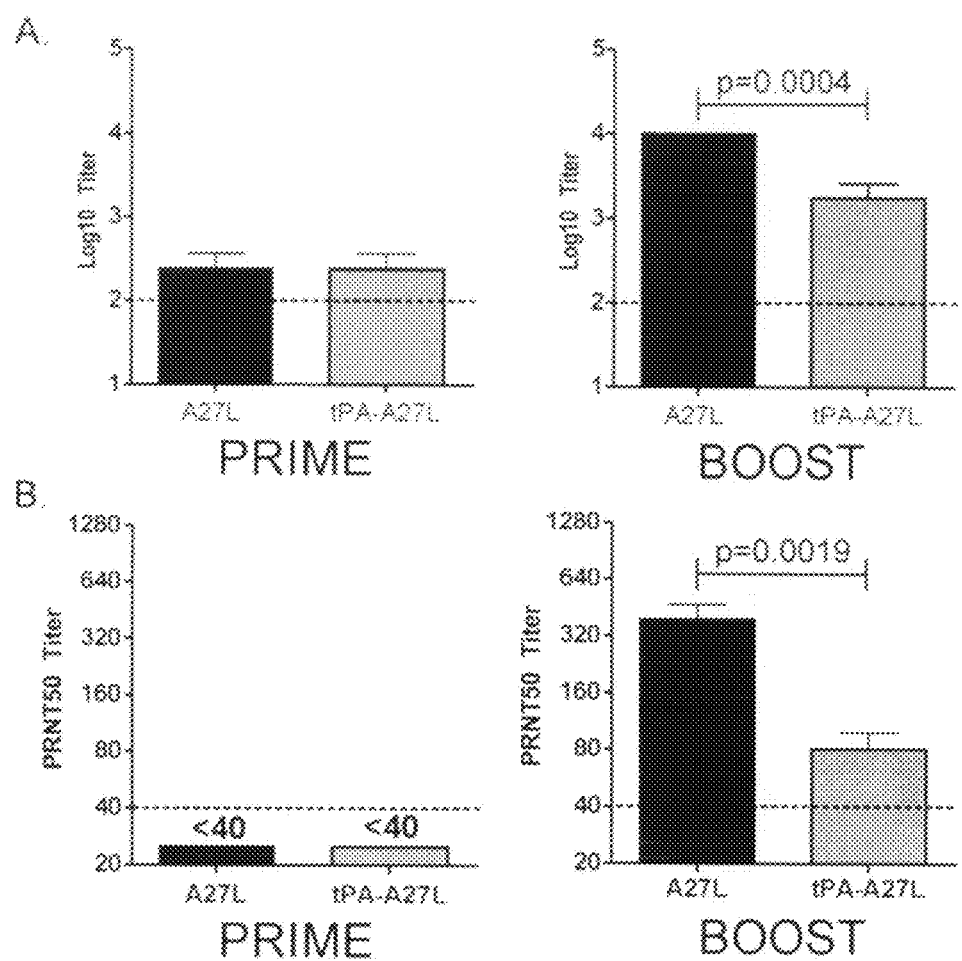
FIG. 2. Antibody responses against A27L in A27L and tPA-A27L in vaccinated mice. A) Purified A27 (50 ng/well) was plated in 96-well plates. ELISAs were preformed using serum from mice vaccinated with A27L or tPA-A27L DNA as described in the legend to FIG. 1A. B) The $PRNT_{50}$ was done as described in FIG. 1B, except the serum used was from A27L- and tPA-A27L DNA-vaccinated mice. These data show that the tPA modification does not enhance the immunogenicity of any gene to which it is linked; rather the tPA modification is immunogen specific.

It was recently reported that the tPA leader sequence can enhance the humoral responses against the orthopoxvirus D8L gene [ref. 19]. The authors found a slight improvement in the protective capacity of tPA-D8L lacking the TM versus D8L. This report, combined with the fact that the tPA leader sequence enhanced the production of antibodies against L1 (FIG. 1) suggests adding this sequence to all of our 4pox vaccine targets would be beneficial. This is further supported by numerous reports demonstrating the positive effects the tPA leader sequence can have on other antigens [ref. 43-48]. However, the ability of the tPA leader sequence to enhance neutralizing antibody production appears to be antigen specific. This conclusion is based from our finding that tPA-A27L did not elicit any increase in antibody responses against the A27 protein (FIG. 2). In fact, we saw about a 0.5 log decrease in ELISA titer and a marked decrease in $PRNT_{50}$ titers when the tPA-A27L was used for vaccination (FIG. 2). It is not clear why tPA-A27L did not lead to enhanced antibody production. A27 is normally found in the cytoplasm of infected cells. Perhaps targeting A27 to the ER modifies the antigen, possibly by glycoslyation, such that important epitopes are disrupted. While it has been reported that tPA enhances the immunogenicity of other immunogens [refs. 19 and 43], our data shows that tPA-A27 does not get enhanced—which demonstrates that tPA's ability to augment an immunogen is more antigen-specific than previously appreciated. The references 19 and 43 actually teach that tPA will enhance everything, but indeed our findings prove otherwise.

Figure 6:
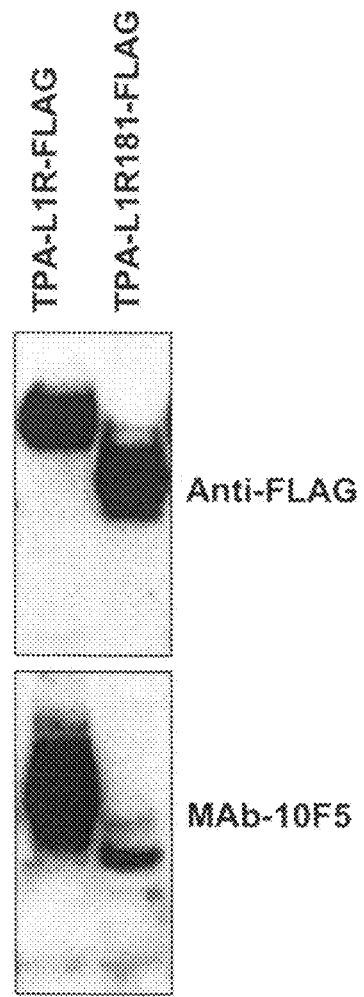
FIG. 6. Western blot showing expression of FLAG-tagged L1R constructs in COS cells. 1×10(6) COS cells were transfected with vectors expressing the indicated L1R constructs or not transfected. 48 h post-transfection COS cell lysates were preparted using tris lysis buffer [10 mM Tris [pH 7.5], 2.5 mM $MgCl_2$, 100 NaCl, 0.5% Triton X-100]. 10% of the lysate, representing 1×10(5) cells was resolved on a 10% gel by SDS-PAGE under reducing (anti-FLAG) or non-reducing (Mab-10F5) conditions. Subsequently the gel was transferred to nitrocellulose membranes and blocked overnight at 4° C. with 5% skim milk in Tris buffered saline containing 0.005% tween (TBS-T). Membranes were washed three times in TBS-T and then incubated with either an Anti-FLAG antibody (1:1000) or an anti-L1 monoclonal antibody Mab-10F5 (1:1000) for 1 h at room temperature in TBS-T containing 5% skim milk. Membranes were then washed three times in TBS-T and incubated with either an anti-Rabbit (anti-FLAG) or anti-Mouse (MAb-10F5) secondary antibody (1:10000) for 45 m at room temperature in TBS-T containing 5% skim milk. Bound antibody was detected by treating the nitrocellulose filters with enhanced chemilumescence detection reagents and exposing the filters to Full Speed Blue X-ray film.
Figure 7A:
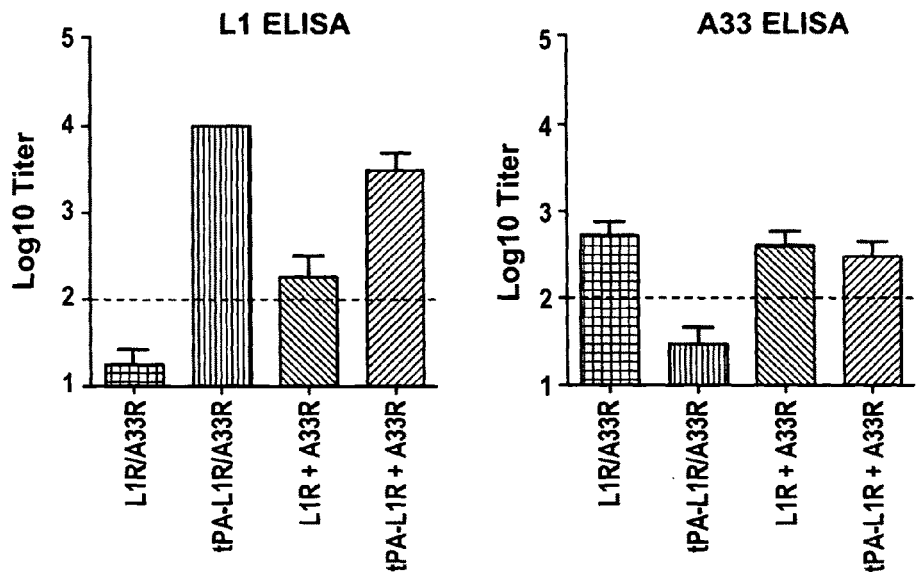
FIG. 7. Antibody responses against A33 and L1 when both genes are on the same carriers. A. Purified L1 (300 ng/well) and A33 (50 ng/well) were plated in the wells of a 96-well plate. Serum from animals vaccinated twice with L1 or TPA-L1R and A33 on the same gold carriers or on different cartridges was examined by ELISA for reactivity both antigens. Serum from vaccinated mice was serially diluted tenfold and incubated with immunogens as described in FIG. 1A. B. Serum from mice vaccinated twice with A33R and L1R or tPA-L1R on the same gold (A33/L1R or A33R/tPAL1R) or different cartridges (A33R+L1R or A33R+tPA-L1R) was serially diluted twofold and incubated with ~50 PFU of VACV strain IHD-J for 1 h at 37° C. Antibody-virus mixtures were adsorbed to confluent monolayers of BSC-1 cells for 1 h at 37° C. After adsorption, a 1:1 mixture or 2×EBME and 3% methocellulose was added to each well. Three days postinfection, plaques were visualized by staining monolayers with 1.5% crystal violet. 50% neutralization titers were calculated relative to the plaque count for virus that was not incubated with serum. Data was plotted as a mean titer for each group +/−standard deviation.
Figure 7B:
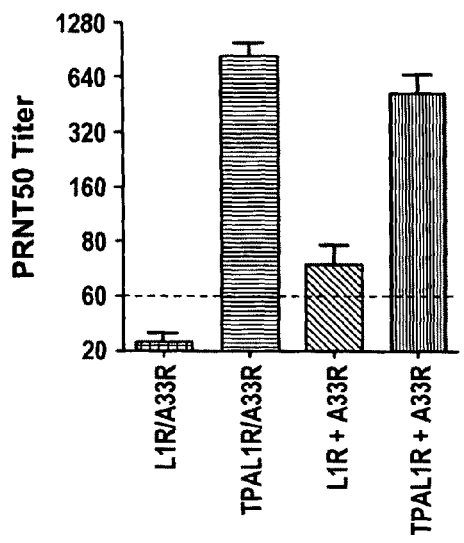
Figure 8A:
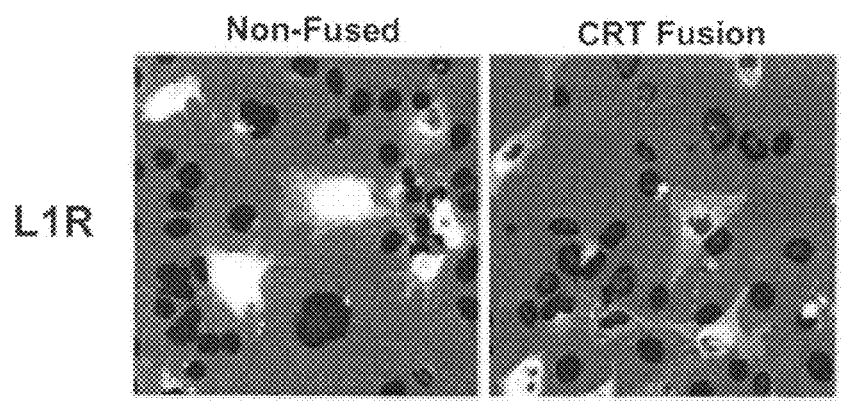
FIG. 8. In vitro expression of the L1 immunogen fused with a codon-optimized tPA-modified or fused with the endoplasmic reticulum targeting protein Calreticulin. A. COS-7 cells were plated on coverslips in 12-well plates and transfected with the indicated gene fused to CRT or not fused (tPA-L1R). 48 h post-transfection, cells were fixed and incubated with the anti-L1 specific monoclonal antibody MAb-10F5 (1:100). Bound antibody was detected using Alexafluor488-anti-mouse (L1, A27 and A33) or Alexafluor488-anti-Rabbit (B5) IgG secondary antibody and fluorescent microscopy (magnification x200). The nuclei were stained with DAPI. B. COS-7 cells were transfected in T25 plates with the indicated L1R gene fused to CRT (black line) or not fused (tPA-L1R) (gray line). 48 h post-transfection, cells were trypsinized, fixed with Cytofix (BD biosciences) and permeablized with perm/wash buffer (BD biosciences). Cells were then incubated for 1 h with MAb-10F5 or a non-specific control antibody (shaded areas) (1:100) in perm/wash buffer. Subsequently, cells were incubated with a secondary Alexfluor488-anti-Mouse (1:500) antibody in perm/wash buffer for 1 h. After washing, stained cells were analyzed by flow cytometry. For each graph, 10000 cells were counted.
Figure 8B:
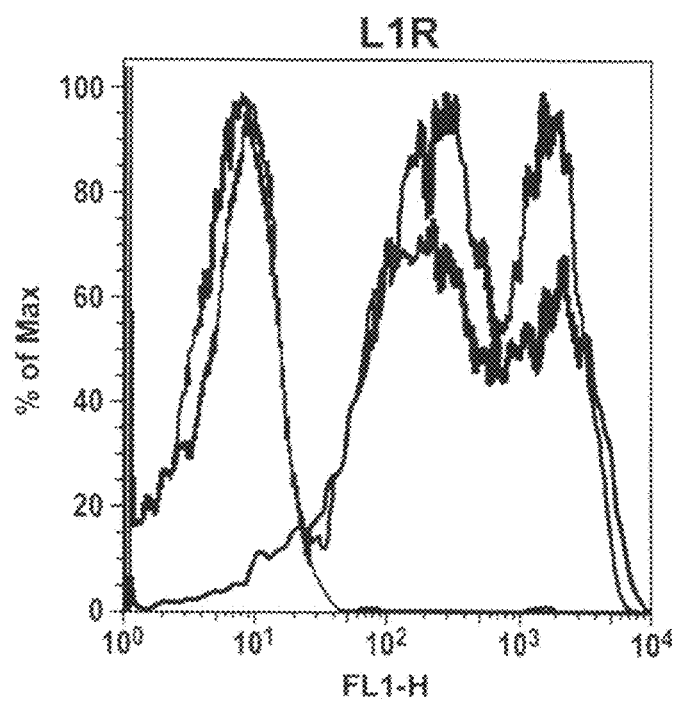
Figure 9:
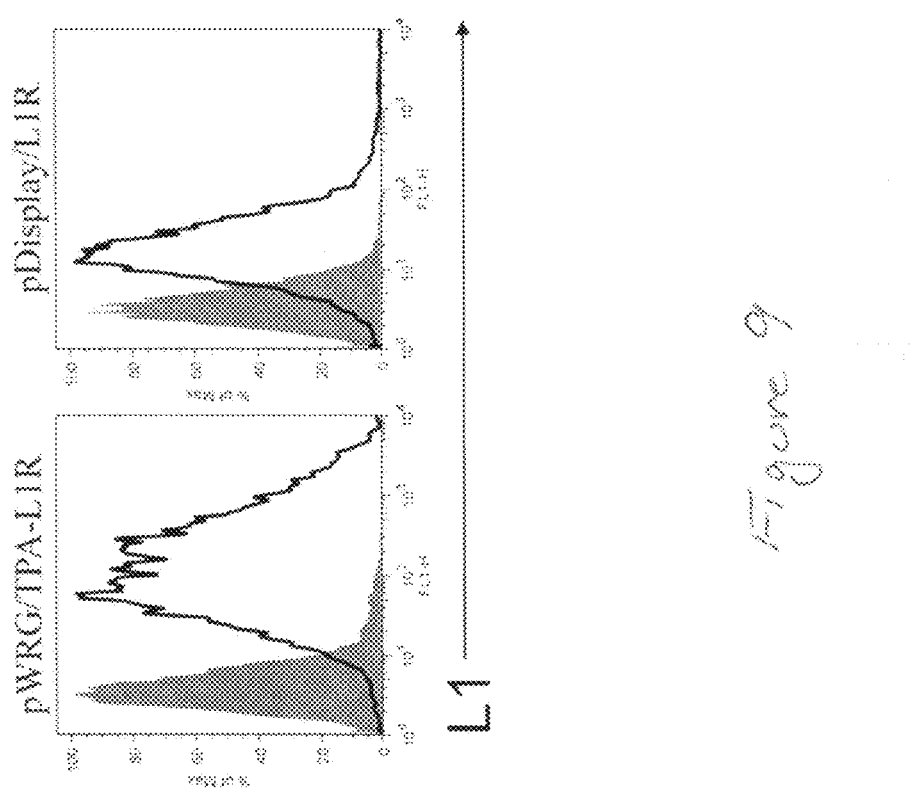
FIG. 9. Expression of L1R from the pDisplay vector. The L1R gene was cloned into the pDisplay vector (Invitrogen). This vector contains a IgG kappa leader sequence which targets proteins to the secretion pathway. The L1R gene PCR amplified using the forward primer GGG GGa gat ctA TGG GTG CCG CAG CAA GC (SEQ ID NO: 7) and the reverse primer GGG ctg cag TCA GTT TTG CAT ATC CG (SEQ ID NO: 8). The PCR product was digested with BglII and PstI, which were incorporated into the primers. The digested molecule was then ligated into the pDisplay vector at these restriction sites. This placed the L1R gene in-frame with the secretion signal. Sequencing was preformed to confirm placement of the L1R gene the vector. COS cells were transfected with either pWRG/TPA-L1R or pDisplay/L1R using fugene6 (Roche). 48 h post-transfection cells expression of surfaced expressed L1 was analyzed by flow cytometry using the anti-L1 monoclonal antibody MAb-10F5 (black line) or a control antibody MAb-10G10 (solid grey line) that recognizes A33. Each analysis screen 10000 cells.

Another advantage we found was the inclusion of the transmembrane (TM) DNA regions in the L1R. For DNA vaccine immunogens, typically the TM regions of the antigen are removed to allow secretion of the molecules into the extracellular milieu. Contrary to this convention, the TM region of L1 was purposefully retained. This was done for several reasons. We found that a secreted version of L1 containing only the ectodomain region did not interact efficiently with potently neutralizing antibodies to the same extent as full-length L1, despite being expressed at similar levels (FIG. 6). Furthermore, Aldaz-Carroll, L., et al were unable to generate neutralizing antibodies that interacted with the epitope recognized by potentially neutralizing antibodies such as MAb-7D11 or 2D5 in mice vaccinated with purified L1 lacking the TM [ref. 42]. Instead, they identified less potent neutralizing antibodies interacting with different epitopes. The failure to generate antibodies interacting with the discontinuous epitope may possibly have been due to glycosylation of the L1 molecule by insect cells. However, removal of the TM region can negatively impact the immunogenicity of other antigens targeted through the secretory pathway. For example, Rath, A. et al found that the presence of the TM domain and a secretion signal sequence on the rabies virus glycoprotein was needed to obtain the highest levels of neutralizing antibody [ref. 44]. This is because in the absence of the TM, the protein fails to fold properly leading to the disruption of the critical epitope [ref. 44]. Hence, for antigens whose antibody epitopes are highly conformationally dependent, such as L1 [ref. 34], retention of the TM region might be critical.

To generate L1 for the purposes of protein purification, Aldaz-Carroll et al used a similar approach and targeted L1 lacking its transmembrane (TM) region to the secretory pathway in insect cells using a melittin signal sequence [ref. 42]. Secreted L1 (lacking the TM region) appears to fold more natively as evidenced by its ability to interact with conformationally dependent antibodies [ref. 42].

Unexpectedly, the inclusion of the transmembrane region also provided the advantage of improving binding of the epitope. The protein that was purified for the Aldaz-Carroll study was for the purposes of a protein vaccine. This molecule lacked the TM region so that it could be more easily purified. The problem with the Aldaz-Carroll results, and the benefit of our invention, is that they failed to generate antibodies that recognized the epitope bound by MA-7D11/MAb-10F5. In addition, upon protein (not gene) vaccination, the antibodies that they obtained were not potently neutralizing (did not neutralize to the same extent as antibodies that interact with the MAb-7D11/MAb-10F5 epitope). Our findings show that by using a full length tPA-L1R, the expressed protein must fold more naturally as we see improved interaction of MAb-10F5 with the molecule compared to tPA-L1R lacking the TM region (western blot data of FIG. 6). By displaying a more native immunogen to the host immune system, one expects to achieve better neutralizing antibody production. And because the epitope is intact, antibodies are assumed to interact with the potently neutralizing region of L1R where MAb-10F5 and MAb7D11 bind.

As noted above, another advantage of retaining the transmembrane region in the L1R was that it resulted in less secretion of the L1 product from the cell, so that it was concentrated at the cell membrane. We concluded that by retaining the TM region, L1 could fold better and a byproduct of having the TM region is that it ended up in the plasma membrane. Others have found that concentration of vaccine immunogens on the cell surface can enhance immunogenicity, at it is likely that this is one reason why the tPA-L1R is so effective at eliciting a neutralizing antibody response (Reddy et al., Virology 189 423-434 [1992]; Srinivasan et al. Infection and Immunity 63:4907-4911 [1995]).

In a previous study, we found that unmodified L1R could protect ~60% of mice against lethal challenge with VACV strain WR after three vaccinations [ref. 20]. In this current application, the L1R group had low $PRNT_{50}$ titers and all mice died from infection. In contrast, the tPA-L1R group had $PRNT_{50}$ titers significantly higher than in previous studies (FIG. 1 and ref. 20, 21). However, despite these high titers, animals in the tPA-L1R group, while surviving a few days longer than the L1R group, all succumbed to infection (FIG. 5).

Figure 14:
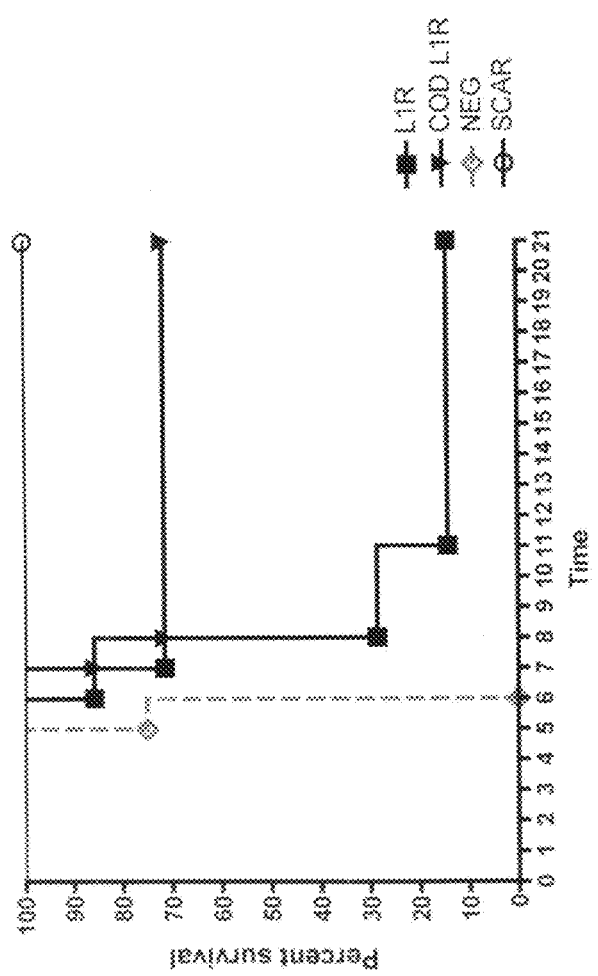

However, we previously reported non-human primate data demonstrating that the unmodified L1R vaccine alone (without other immunogens present) showed some level of protection, although the animals did show signs of the disease, even severe symptoms [ref. 22]. Thus, it is reasonable to conclude that a stand-alone tPA-L1R vaccine will elicit enhanced neutralizing antibody levels and therefore further reduce signs of disease. It is more desirable, of course, that a vaccine protect both against mortality and symptoms—but tPA-L1R alone (in the absence of other immunogens) may function as a stand-alone vaccine, albeit not the preferred version of our vaccine embodiment. We have data showing that the codon-optimized tPA-L1R provided more protection in mice compared to wild-type tPA-L1R, where 70% of the codon-optimized tPA-L1R vaccinated mice survived, but only ~10% of wild-type tPA-L1R vaccinated mice survived. All of the animals showed significant weight loss. This supports our previous non-human primate data that L1R alone can function as a vaccine, albeit the animals still get severe disease (and some may die). (See FIG. 14.).

Thus, we can reasonably expect that mammals vaccinated with tPA-L1R alone may get symptoms of the disease, but survive, whereas animals getting tPA-L1R and at least one of A33 or B5R (and even more preferred, all three of A33, B5R and A27L) would both survive and show no or little signs of the disease. In the art of vaccines, compositions may qualify as "vaccines" where there is less than 100% protection or no disease. Thus, our vaccines comprising tPA-L1R alone in the absence of other poxvirus immunogens would function as a vaccine, albeit with reduced effectiveness as the animals (humans) would likely get severe disease (but still survive). In addition, it is preferred that the tPA-L1R vaccine be administered in at least three, and more preferably four or more times.

It is noted that tPA-L1R alone is an excellent immunogenic composition. It consistently raises potent levels of neutralizing antibody, as our data shows. Such compositions are quite useful for another embodiment of our invention: generating neutralizing antibody in humans and/or other animals (ducks, rabbits) for the purpose of functioning as a immunotherapeutic.

In previous studies, mice were challenge by the intraperitoneal route with VACV strain WR [ref. 20, 21], whereas in this current study mice were challenge i.n. with VACV strain IHD-J. The latter model involves a lower challenge dose and requires more in vivo dissemination of virus as evidenced by the extended time course of disease. IMV neutralizing antibodies are insufficient to protect in this model unless the response is potent enough to reduce the initial exposure below a critical level (Hooper, unpublished data). If this doesn't occur, then IMV-infected cells produce EEV, and this progeny virus disseminates unabated resulting in lethal disease, usually by day 6. If anti-EEV antibodies are present, then it is believed that dissemination is prevented and protection is achieved.

The issues involved with vaccination using L1 alone highlights the preference of targeting both infectious forms of orthopoxviruses. We, and others, have shown that vaccines comprised of combinations of immunogens targeting both infectious forms of orthopoxvirus, IMV and EEV, provides superior protection versus targeting only IMV or EEV [ref. 19-24, 41, 50, 51]. IMV neutralizing antibodies, including those against L1 and A27, neutralize virus in the initial exposure and also can eliminate any IMV released from infected cells that are lysed or EEV that are disrupted. It is unclear how anti-EEV antibodies protect, including those against A33 and B5, however the mechanism(s) likely involves the prevention of EEV spread within the host and possibly the elimination of infected cells by processes involving complement and/or Fc-receptor bearing cells. In previous studies, protection elicited by a protein or DNA vaccine targeting both infectious forms required three or four vaccinations.

Recently, it was shown in mice that purified L1 and A33 proteins could elicit a protective antibody response after only two vaccinations if certain adjuvants were used [ref. 50]. This study used purified proteins and an adjuvant. The protein vaccination by itself was not immunogenic and required an immune simulator (i.e. adjuvant) to elicit a response.

In gene-based vaccines such as ours, it is known that L1R and A33R interfere with each other—this is unique to gene-based vaccines, where the molecules are expressed in the same cell type from a gene. In reference 50, the protein for the vaccine in reference 50 was made separate, an L1 batch and an A33 batch and then combined as protein (not DNA) for the vaccination; there was no problem with L1 and A33 interference in reference 50. As noted above, we were surprised that modified L1R and A33 could be co-delivered on the same carrier particle in gene-gun vaccination, without interferences.

In addition, unlike the protein vaccine of reference 50, our vaccine requires no adjuvant to be sufficiently immunogenic. The fact that we did not need adjuvant to elicit an immune response shows an advantage of a gene-based orthopoxvirus vaccine (consisting of tPA-L1R and an EEV immunogen (A33) and optionally another IMV (A27L) and EEV target (B5R). Here, we demonstrated that delivery of the 4pox antigens, in the absence of adjuvants, could generate protective immune responses after only two vaccinations (FIGS. 4 and 5 and Table 1). This is the first report demonstrating that a subunit orthopoxvirus vaccine can protect against lethal challenge after only two vaccinations, without requiring the addition of adjuvant. Again, this was a surprise since we had no idea if the vaccine would protect in the absence of an adjuvant until we saw that it elicited a good antibody response and was protective.

Moreover, substitution of tPA-L1R for unmodified L1R DNA provided statistically greater protection from challenge (FIG. 5). The enhanced protection was probably attributable to higher amounts of anti-L1 capable of neutralizing input virus and lowering the initial viral load in infected animals. This could not have been predicted based on our previous studies with tPA-L1R, since it was equally possible that tPA-L1R would traffic in cells (or in the host in general) in such a way that it would be no more immunogenic than unmodified L1R. Surprisingly, the amount of neutralizing antibody the tPA-L1R construct was able to produce was significant and potent.

TABLE 1

Immunogenicity data for individual mice vaccinated with 4pox or pox(tPA-L1R)[a]

| | PRIME | ELISA[b] | | | | BOOST | ELISA[b] | | | |
|---|---|---|---|---|---|---|---|---|---|---|
| Mouse ID | PRNT50 | L1 | A33 | B5 | A27 | PRNT50 | L1 | A33 | B5 | A27 |
| 4pox | | | | | | | | | | |
| 773 | 20 | 1 | 1 | 2 | 2 | 80 | 1 | 3 | 3 | 4 |
| 815 | 20 | 1 | 1 | 2 | 2 | 20 | 1 | 2 | 3 | 3 |
| 775 | 20 | 1 | 2 | 2 | 2 | 40 | 1 | 3 | 3 | 4 |
| 776 | 20 | 1 | 2 | 2 | 3 | 320 | 3 | 4 | 4 | 4 |
| 777 | 20 | 1 | 1 | 3 | 2 | 20 | 2 | 3 | 3 | 4 |
| 778 | 20 | 1 | 1 | 2 | 2 | 40 | 1 | 1 | 3 | 4 |
| 779 | 20 | 1 | 2 | 1 | 3 | 160 | 1 | 3 | 3 | 4 |
| 780 | 20 | 1 | 1 | 1 | 3 | 40 | 1 | 2 | 3 | 4 |
| 4pox(tPA-L1R) | | | | | | | | | | |
| 781 | 20 | 2 | 1 | 2 | 3 | 640 | 3 | 2 | 4 | 5 |
| 782 | 20 | 1 | 1 | 3 | 2 | 1280 | 3 | 2 | 4 | 4 |
| 783 | 20 | 2 | 1 | 2 | 2 | 640 | 3 | 1 | 3 | 4 |
| 784 | 20 | 2 | 1 | 2 | 2 | 640 | 3 | 2 | 3 | 4 |
| 785 | 20 | 1 | 1 | 2 | 3 | 160 | 3 | 3 | 3 | 4 |

TABLE 1-continued Immunogenicity data for individual mice vaccinated with 4pox or pox(tPA-L1R)[a]

| Mouse ID | PRIME | ELISA[b] | | | | BOOST | ELISA[b] | | | |
|---|---|---|---|---|---|---|---|---|---|---|
| | PRNT50 | L1 | A33 | B5 | A27 | PRNT50 | L1 | A33 | B5 | A27 |
| 786 | 20 | 1 | 1 | 2 | 2 | 640 | 3 | 1 | 4 | 4 |
| 787 | 20 | 1 | 2 | 2 | 3 | 640 | 3 | 2 | 3 | 4 |
| 788 | 20 | 1 | 1 | 2 | 2 | 320 | 3 | 1 | 4 | 4 |

[a]Mice were vaccinated with the indicated genes delivered on separate cartridges. Mice were vaccinated with one cartridge per gene.
[b]ELISAs were performed using the purified protein for each orthopoxvirus antigen.

As described herein, some of the embodiments of our invention may be used for humans and animals as a component of a gene-based vaccine (e.g., DNA vaccine, virus-vectored vaccine) against orthopoxviruses, whose members include biological weapons threats (variola virus and monkeypox virus).

As described herein, the compositions of this invention may also be used to generate highly potent neutralizing antibodies (e.g., by DNA vaccination) in various animals (humans, humanized rabbits and mice or ducks whose antibodies lack functional Fc regions). These antibodies could then be used in other humans or animals as an anti-poxvirus therapeutic (pre/post exposure). This use would be a vaccinia immunoglobulin replacement.

The vaccines and compositions of our invention could also be used as a priming vaccine for use in humans to attenuate the side effects associated with use of live-vaccinia virus vaccination (the Dryvax product).

As detailed below, we conducted numerous and comprehensive testing in the development of our invention. Some results can be summarized as follows.

We were able to prove that full-length tPA-L1 interacts with neutralizing anti-L1 monoclonal antibodies (Mab-10F5) with much greater efficiency compared to a truncated soluble version (tPA-L1R1-181). This was shown by western blot. This experiment involved the generation of a FLAG tagged version of tPA-L1R and tPA-L11-181 and showed that, despite being expressed to similar levels, the tPA-L1 interacts much more efficiently with conformational dependent, potently neutralizing antibodies (Mab-10F5). Thus, the full-length version of L1R was chosen for use in vaccine development rather than a truncated soluble form.

The above experiment also showed that L1R without the tPA sequence is expressed poorly in transacted cells, most likely because improperly folded L1R gets degraded within the cell.

One important finding was proof that tPA-L1R DNA is a better immunogen compared to L1R DNA. Mice were vaccinated by gene-gun twice at a three-week interval with tPA-L1R or L1R DNA. ELISAs showed that mice vaccinated with tPA-L1R produced a much higher level of anti-L1 antibody after two vaccinations. Plaque reduction neutralization tests demonstrated that the level of neutralizing antibodies was greater in the mice vaccinated with tPA-L1R.

We proved that other vector systems work for delivery of the tPA-L1R gene was derived. Venezuelan equine encephalitis (VEE) replicons (VRPs) expressing the tPA-L1 R were produced. Two different VEE-replicon backbones were used. An experiment was performed comparing the immunogenicity of tPA-L1R versus L1R in mice. After a single dose, the tPA-L1R VRPs elicited a significantly higher level of neutralizing antibodies than the L1R VRPs.

Advantages and Unexpected Results:
A tPA Leader Sequence Enhances the Neutralizing Antibody Responses Against L1.

We previously showed that adding a tPA leader sequence to the L1R gene leads to an enhanced interaction of the L1 molecule with conformationally-dependent and potently neutralizing antibodies (MAb-10F5 and MAb-7D11) [ref. 23]. Based on these findings, we conducted an experiment to determine if this construct could generate a more robust neutralizing antibody response in mice vaccinated by gene-gun. Groups of eight BALB/c mice were vaccinated by gene-gun with DNA encoding either unmodified L1 or tPA-L1. Three weeks after the prime, mice were boosted. Anti-L1 antibody responses were assessed by ELISA with purified L1. Antibody responses in mice vaccinated with the unmodified L1R gene were below the level of detection after the priming vaccination (FIG. 1A). In contrast, mice vaccinated with tPA-L1R DNA had detectable anti-L1 antibodies after the prime, with a titer of ~2. After the boost, antibody responses induced by both modified and unmodified L1 increased to 3.7 and 2.6 log titers, respectively. The anti-L1 response in tPA-L1R vaccinated animals was significantly greater (p<0.05) than mice vaccinated with unmodified L1R after both the prime and the boost.

We also tested the capacity for anti-L1 antibodies to neutralize VACV in a PRNT. The 50% neutralizing titers (PRNT50s) correlated with the titers observed in the ELISA. After the initial vaccination, PRNT50s for both groups were below the level of detection (FIG. 1B). There was significant neutralizing activity associated with the serum from tPA-L1R-vaccinated mice after the boost and the mean PRNT50 titer for this group was over 550. The mean PRNT50 titer in the unmodified L1R-vaccinated mice was ~14-fold lower. This difference was significant (p<0.05). These findings clearly indicated that adding the tPA leader sequence greatly enhanced the neutralizing antibody response against L1.

The tPA Leader Sequence does not Enhance Production of Neutralizing Antibodies Against the A27 Protein.

Adding a tPA leader sequence enhances the immunogenicty of several DNA vaccine immunogens, including the orthopoxvirus molecule D8L [ref. 19]. Therefore, we tested the capacity of the tPA leader sequence to enhance the antibody response against A27, a protein on the surface of IMVs, beneath the envelop of EEVs [ref. 39] and a component of our 4pox vaccine [ref. 21]. As determined by ELISA with purified A27, after the initial vaccination there was little difference in anti-A27 antibody responses between mice vaccinated with either A27L or tPA-A27L, and both groups had titers ~2.2 (FIG. 2A). This level of anti-A27 antibody did not neutralize virus (FIG. 2B). Similar to the L1R and tPA-L1R groups (FIG. 1A), ELISA titers for both A27L- and tPA-A27L-vaccinated mice increased after the boost. However, A27L-vaccinated mice had antibody titers that were ~0.5 logs higher than those of the tPA-A27L-vaccinated mice. This difference was statistically significant ($p<0.05$). This more robust anti-A27 antibody response correlated with a more significant $PRNT_{50}$ titer ($p<0.05$), which was ~320 compared to the $PRNT_{50}$ titer of tPA-A27L-vaccinated mice, which was below 80. These findings demonstrated that enhanced antibody responses gained by adding the tPA leader sequence to the L1R gene, did not occur with A27L.

Adding the tPA Leader does not Impact the IgG Isotype Against L1.

Figure 3:
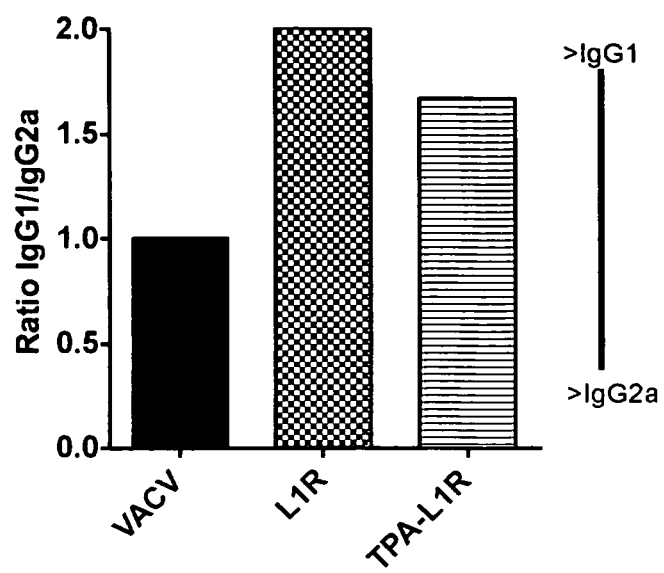
FIG. 3. IgG isotypes in vaccinated animals. Pooled serum from either VACV-infected mice or mice vaccinated with L1R, tPA-L1R, A27L, and tPA-A27 was serially diluted tenfold. Dilutions were incubated with two plates each containing either purified L1 (L1R and tPA-L1R vaccinated mice) or purified A27 (A27L- and tPA-A27L-vaccinated mice). Secondary anti-mouse antibodies conjugated to HRP and specific for either IgG1 or IgG2a were then incubated with the samples. ABTS was added to each well and reactions were terminated using 5% SDS. Endpoint titers for each secondary antibody were calculated as described in the materials and methods. The ratio of IgG1 to IgG2a was determined and plotted.

Typically, epidermal vaccination by gene-gun leads to a Th2 response characterized by the production of IgG1 antibodies [ref. 40]. As such, trafficking of L1 from the cytoplasm to the secretion pathway, which targets molecules through the endoplasmic reticulum and golgi, could have affected the type of immune responses elicited against this molecule. Therefore, it was possible that in animals vaccinated with tPA-L1R, there might be a more significant activation of the Th1 arm of the immune response. To investigate this possibility, serum from mice vaccinated with tPA-L1R or unmodified L1R DNA was incubated with purified L1 and then incubated with an isotype-specific secondary antibody. As shown in FIG. 3, there was little change in the ratio of IgG1 to IgG2a antibodies between L1R and tPA-L1R vaccinated mice. Antibody responses in both groups were skewed towards a IgG1 response, whereas a more balanced response was observed using hyperimmune serum from mice infected with VACV (FIG. 3). Thus, adding the tPA leader signal to L1R does not impact isotype preference generated following gene-gun delivery.

The tPA Leader Sequence Enhances Antibodies Against L1 in Mice Vaccinated with a Multi-Gene Combination.

Figure 4:
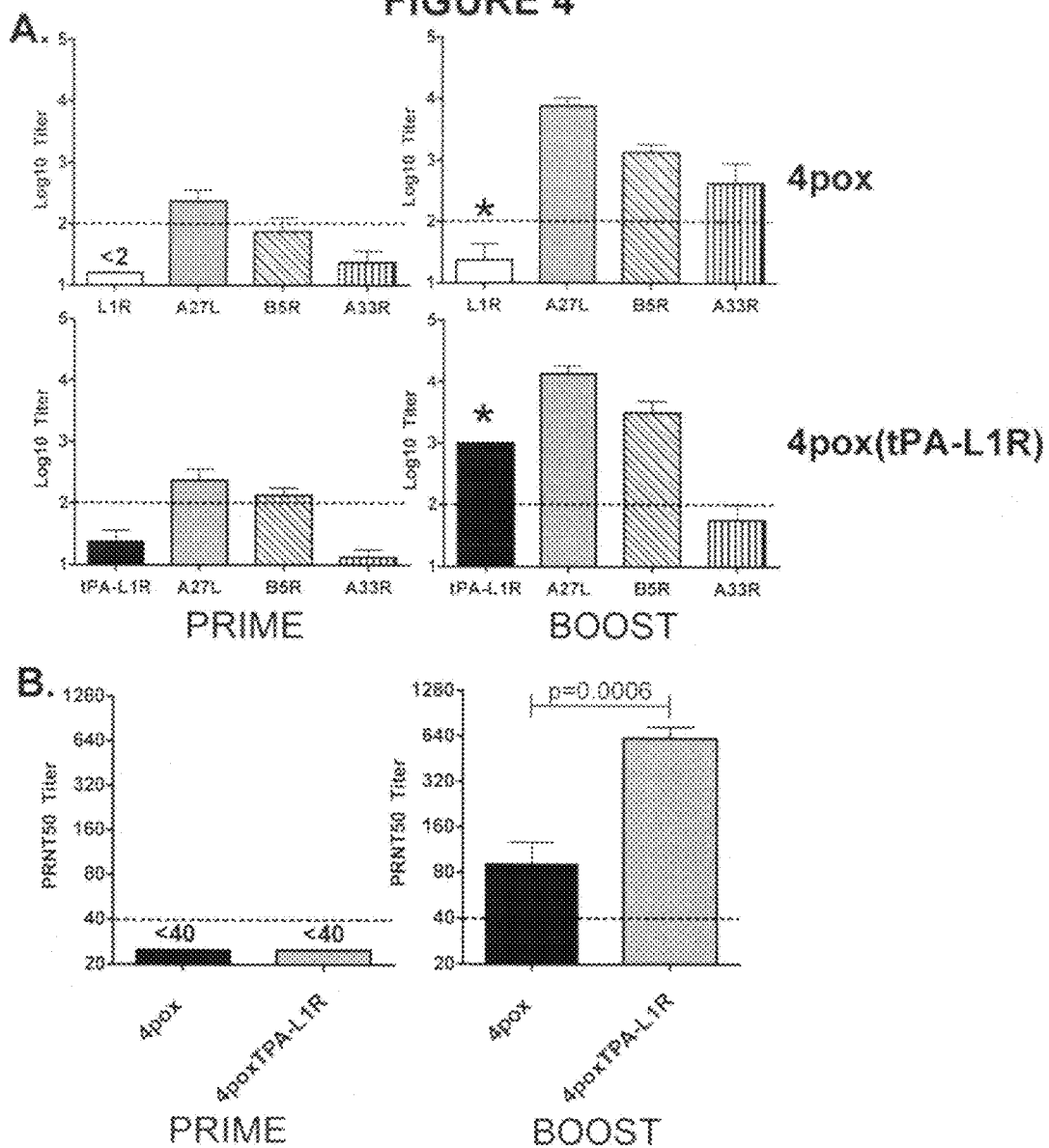
FIG. 4. Antibody responses against B5, A33, A27 and L1 in DNA vaccinated mice. A) Mice were primed with all four immunogens (B5R, A33R, A27L, and L1R or tPA-L1R) and boosted 3-weeks later with the same molecules as indicated. Serum from vaccinated animals (prime and boost) was examined by ELISA for reactivity with all four immunogens. Serum from mice was serially diluted tenfold and incubated with immunogens as described in FIG. 1A. The asterisk denotes that the anti-L1 antibody response was significantly greater (p=0.00002) for the 4pox(tPA-L1R) group following the boost, all other antibody responses were statistically insignificant (p>0.05000). B) The presence of neutralizing antibodies in mice vaccinated with all four antigens was assessed by PRNT. The lowest dilution tested was 1:40 (dashed-line indicates limit of detection).

To ensure adequate cross-protection and reduce the potential for a genetically modified virus to bypass protection of a subunit vaccine, our candidate molecular vaccine targets multiple antigens present on both infectious forms of orthopoxviruses, the EEV (A33 and B5) and IMV (L1 and A27). Therefore, we next examined if there was an enhancement in neutralizing antibody production against L1 when the unmodified L1R gene was substituted with tPA-L1R in mice vaccinated by gene-gun against all four antigens in mice (4pox vaccine). Mice were primed with DNA encoding all four immunogens (A33, B5, A27 and L1, or tPA-L1) and then boosted three weeks later using the same combinations. Antibody responses against the four targets were then assessed by ELISA with purified VACV proteins. We observed that L1 antibody responses in mice vaccinated with 4pox were below the level of detection after the prime and only two mice developed detectable antibodies against L1 after the boost (FIG. 4A and Table 2). Antibody responses against the other three antigens were detected after the boost (FIG. 4A and Table 1). Among these responses, A27 was the most robust, while A33 was the weakest. After the initial vaccination, three mice in the 4pox(tPA-L1R) group had detectable L1 antibody responses and all mice developed anti-L1 titers of 3 logs after the boost (FIG. 4A and Table 1). Antibody titers against B5 and A27 were also detectable in mice after the boost. However, some mice did not develop anti-A33 responses and even after the boost, three of the eight mice had anti-A33 responses below the level of detection (Table 1). Of these data, only the anti-L1 response after the boost was significantly different between the 4pox and 4pox(tPA-L1R) groups ($p<0.05$). Responses against B5, A27 and A33 were all found to be statistically insignificant ($p>0.05$).

The neutralization responses elicited by 4pox or 4pox(tPA-L1R)-vaccinated mice were also evaluated. Neither the 4pox nor the 4pox(tPA-L1R) had a $PRNT_{50}$ titer after the prime. However, neutralizing responses were observed for both groups after the boost (FIG. 4B and Table 1). Among these responses, the $PRNT_{50}$ was ~sevenfold higher in mice vaccinated with 4pox(tPA-L1R). This was a significant difference ($p<0.05$). These findings demonstrated that when tPA-L1R was substituted for the unmodified L1R gene, the 4pox DNA vaccine elicited antibody responses against L1 and the three other antigens (B5, A33 and A27) after only two vaccinations.

Improved Protection in Mice Vaccinated with a Multi-Gene Combination Containing tPA-L1R.

Mice were vaccinated two times with L1R, tPA-L1R, 4pox, or 4pox(tPA-L1R) and then challenged intranasally with three $LD_{50}$ of VACV strain IHD-J. For controls, two groups of mice either unvaccinated or vaccinated with live-virus (Connaught) by tail scarification were also challenged. Weights were monitored for 14 days postinfection. As shown in FIG. 5, unvaccinated mice began to lose weight on day 2 and by day 7, all mice died. Mice vaccinated with unmodified L1R also began to lose weight on day 2 and all mice succumbed to infection by day 7. Mice vaccinated with tPA-L1R survived longer; nevertheless, all mice in this group died by day 11. We observed greater protection in mice vaccinated with multi-gene combinations compared to those vaccinated with single genes. Mice vaccinated with the 4pox vaccine had a transient loss in weight reaching a maximum of ~18% by day 5. Weight of the 4 pox-vaccinated mice started to increase on day 7; however, on day 14 weight remained ~11% below starting weight. Mice vaccinated with 4pox(tPA-L1R) were better protected from VACV challenge (FIG. 5). Weight loss for this group was less severe compared to that of the 4pox group and by day 14, weights in this group were only 5% below starting weight. The difference in weight loss between the 4pox and 4pox(tPA-L1R) groups were significant from day 3 to day 14 ($p<0.05$). As expected, mice vaccinated with live virus had a very transient weight loss that was maximal at day 4 and all the mice survived infection. These findings demonstrated that mice vaccinated with the 4pox molecular vaccine were better protected from lethal challenge with VACV when the tPA-L1R gene was substituted for the unmodified L1R gene.

TPA-L1R can be Used to Generate High-Titer Neutralizing Antibodies in Rabbits Vaccinated by Muscle Electroporation.

Figure 13:
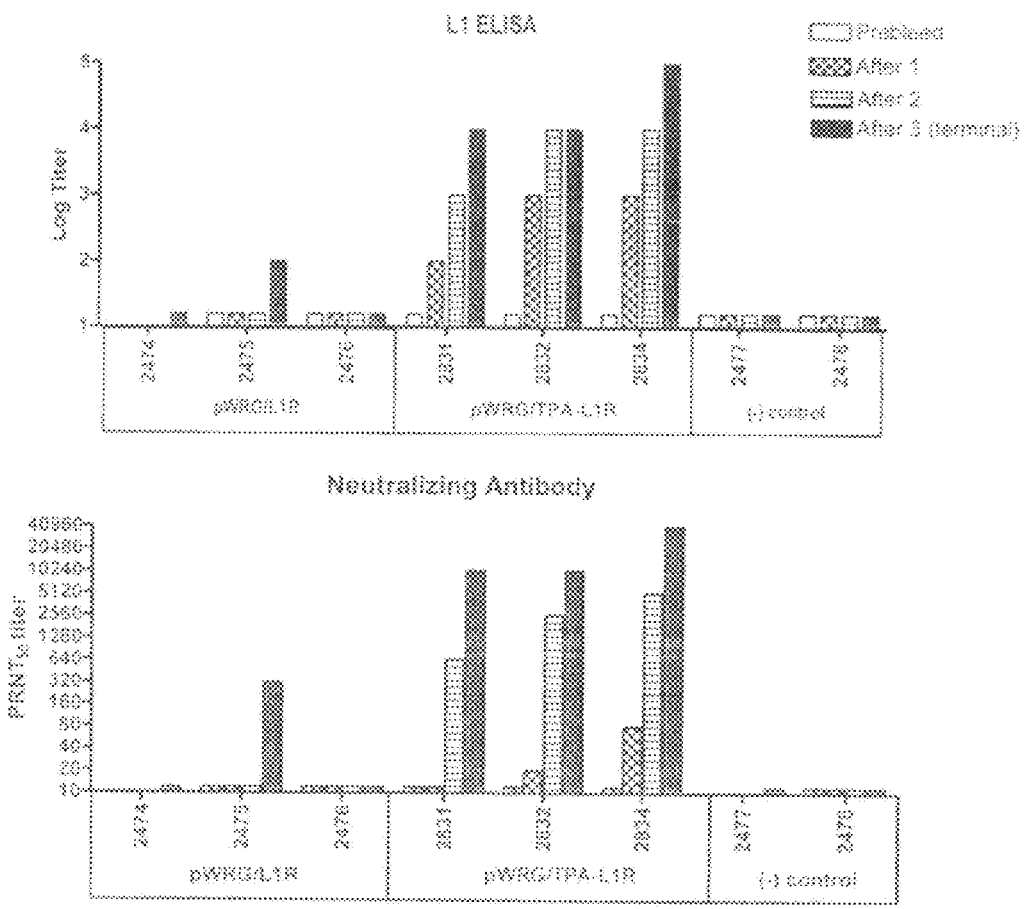

Antibodies against L1R can protect animals from lethal challenge when passively administrated prior to or soon after challenge. Thus, anti-L1 antibodies, in combination with antibodies against other poxvirus molecules, may be a valuable tool that could be used to treat deleterious effects of the smallpox live virus vaccine (e.g. Dryvax), or as an immunotherapeutic against poxviruses outbreaks. The original pWRG/L1R worked very poorly in rabbits to generate high-titer neutralizing antibodies. We sequenced the pWRB/L1R plasmid and found it was intact, and concluded the problem in immunogenicity was not a technical glitch. We investigated if the TPA-L1R DNA elicited more significant neutralizing antibody responses in rabbits vaccinated by electroporation. Rabbits were electroporated with DNA expressing either L1R or tPA-L1R three times at about 4 week intervals. After each immunization, serum was collected and tested for LI binding activity by ELISA and VACV neutralizing antibodies by PRNT. When pWRB/L1R was used, the amount of anti-LI antibody elicited was low and only one of three animals demonstrated neutralizing antibodies (FIG. 13). In sharp contrast, rabbits vaccinated with tPA-L1R had a robust LI response including high-titer neutralizing antibodies. One animal had a PRNT50 titer of approximately 40,000. Our new construct was much more effective at eliciting anti-L1 neutralizing antibodies by muscle electroporation in rabbits than the original construct. These findings demonstrated that the TPA-L1R construct can be used to generate potently neutralizing anti-poxvirus antibodies. Such antibodies are useful in compositions for immunotherapeutics in both humans and mammals. For instance, this plasmid can be used in methods to produce in animals human-safe polyclonal anti-L1 high titer neutralizing antibodies. Plasmids using other endoplasmic-reticulum targeting signals, such as those discussed above, can also be effective for producing in animals human-safe polyclonal anti-L1 high titer neutralizing antibodies.

The invention is described in more detail by the following non-limiting examples.

EXAMPLES

Materials and Methods

Cells and Viruses.

VACV Connaught vaccine strain (derived from the New York City Board of Health strain), VACV strain WR (ATCC VR-1354), and VACV strain IHD-J (obtained from Dr. Alan Schmaljohn) were all maintained in VERO cell (ATCC CRL-1587) monolayers grown in Eagle's minimal essential medium, containing 5% heat-inactivated fetal bovine serum (FBS), 1% antibiotics (100 U/ml penicillin, 100 μg/ml of streptomycin, and 50 μg/ml of gentamicin), 10 mM HEPEs (cEMEM). COS-7 (COS) cells (ATCC CRL-1651) were used for transient expression experiments. BSC-1 cells (ATCC CCL-26) were used for plaque reduction neutralization assays (PRNT). Both BSC-1 and COS cells were also maintained in cEMEM.

Cloning.

The generation of pWRG/tPA-L1R was previously described [ref. 23]. Essentially the L1R open reading frame was subcloned into the NheI and BglII sites of pWRG/tPA vector. This vector contains the tPA leader sequence. To construct the pWRG/tPA-A27L, the A27L open reading frame was subcloned into the NheI and BglII sites of pWRG/tPA. A27L was amplified by PCR using the forward primer 5'-GGGGGGCTAGCATGGACGGAACTCTTTTCC CCGG-3' (SEQ ID NO:5) and the reverse primer 5'-GGGAGATCTTTACTCATATGGACGCCGTCC-3' (SEQ ID NO:6). These primers contain a NheI and BglII site, respectively. The resultant PCR product was cut with NheI and BglII, gel purified, and ligated into pWRG/tPA, in frame with the tPA signal sequence. Sequence analysis confirmed that the A27L insert was in frame with the tPA signal sequence.

DNA Vaccination with Gene-Gun.

The DNA vaccination procedure has been described [ref. 20, 38]. Briefly, plasmid DNA was precipitated onto ~2-μM diameter gold beads at a concentration of 1 μg DNA/1 mg of gold. This DNA-gold mixture was coated on the inner surface of irradiated Tefzel tubing and the tubing was cut into 0.5-in cartridges. Each cartridge contained ~0.25-0.5 μg of DNA coated on 0.5 mg of gold. All cartridges were quality controlled to ensure the presence of DNA. For vaccinations, the abdominal fur of BALB/c mice was shaved and DNA-coated gold was administered using a gene-gun (Powderjet delivery device, Powderject, INC) and compressed helium at 400 p.s.i. to non-overlapping sites. Mice vaccinated with single genes were vaccinated with two cartridges containing the respective gene (0.5 μg-1.0 μg of DNA/dose) at both the prime and boost. Mice receiving multiple genes were vaccinated with one cartridge for each gene at non-overlapping sites (0.25 μg-0.5 μg of DNA/gene/dose) at both the prime and boost. In all experiments, the boost was preformed three weeks after the priming vaccination. All mice were at least 7-9-weeks old at the start of vaccination.

DNA Vaccination by Electroporation

This method of electroporation has been described previously (Hooper et al. 2008). The DNA (1 mg/ml in PBS) was administered bilaterally as 200-μl doses to the gluteus superficialis of the hind limbs of NZW rabbits. The Inovio (San Diego, Calif.) "Twin Injector" electroporation device (a prototype of the Elgen™ system) was used in all instances. Briefly, 100 μl of the buffered DNA was injected into the muscle through each needle (21 ga) of the electrode pair, followed by six pulses at 250 mA, and repeated on the other limb. The rabbits were bled for serum from the central ear artery after before vaccination and then after 1, 2, and 3 vaccinations.

Scarification.

Scarification was preformed by placing a 10-μl drop of phosphate-buffered saline (PBS) containing $8\times10^6$ PFU of VACV (Connaught) near the base of the tail on each mouse. The tail was then scratched ~15-20 times using a needle on a tuberculin syringe.

ELISA Using Purified Proteins.

Histidine-tagged VACV antigens L1 (300 ng/well), A33 (50 ng/well), B5 (50 ng/well), and A27 (50 ng/well), produced in *Escherichia coli* or mammalian cells (B5 antigen produced in baby hamster kidney cells) and purified on nickel columns, were diluted in 0.1 M carbonate buffer [ref. pH 9.6] and plated in duplicate in the wells of a high-binding, 96-well plate (Corning; Corning, N.Y.). The constructs used to produce these ELISA antigens will be reported elsewhere. To control for background, plates were also coated with an irrelevant protein purified over nickel columns (botulinum toxin at 50 ng/well). Plates were blocked for 1 h with PBS with 0.05% tween (PBS-T) and 5% milk. Mouse sera were serially diluted tenfold (starting from 1:100) in PBS-T containing 5% milk and *E. coli* lysate. Serum dilutions were incubated with the purified VACV antigens for 1 h at 37° C. Plates were washed four times in PBS-T and incubated with an anti-mouse IgG conjugated to horseradish peroxidase (HRP) (Sigma) (1:1000) for 1 h at 37° C. Plates were washed again four times in PBS-T and 100 μL of 2,2'-azinobis-3-ethylbenzthiazoline-6-sulfonic acid (ABTS) substrate (KPL, Gaithersburg, Md.) was added to each well. Reactions were stopped by adding 100 μl of ABTS stop solution of 5% (w/v) sodium dodecyl sulfate. The optical density (O.D.) at 405 nm was read on a Spectramax ELISA plate reader (Molecular Devices; Sunnyvale, Calif.). End-point-titers were determined as the highest dilution with an absorbance value greater than the mean absorbance value from negative control plasmid-vaccinated animals plus three standard deviations. Mean titers for individual mice were plotted ±standard deviation.

IgG Isotype ELISA.

Antibody isotyping was determined for mice vaccinated with L1R, tPA-L1R, A27L, and tPA-A27L with purified L1 or A27 protein essentially as described above. To determine the subclass, secondary antibodies (conjugated to HRP) against IgG1 (1:1000) and IgG2a (1:1000) (Bethyl laboratories; Montgomery, Tex.) were incubated with duplicate plates. The ratio of IgG1/IgG2a was calculated and graphed.

PRNT.

The plaque-reduction and neutralization assay (PRNT) was described previously [ref. 20]. Briefly, VACV strain IHD-J was diluted in cEMEM to give ~250 plaque-forming units (pfu)/ml. Aliquots of this viral suspension (100 μl) were incubated with an equal volume of serum diluted in cEMEM for 1 h at 37° C., then 180 µl of sample was adsorbed to confluent BSC-1 cell monolayers in 6-well plates for 1 h in a 37° C. 5% $CO_2$ incubator. All serum samples were heat activated at 56° C. for 30 m before being diluted. Plates were rocked ~15 m. After adsorption, a 2-ml semisolid overlay (Earle's basal minimal essential medium, 1.5% methyl cellulose, 5% heat inactivated FBS, antibiotics (100 U/ml penicillin, 100 µg/ml of streptomycin, and 50 µg/ml of gentamicin) was added to each well. After 4 days in a 37° C. 5% $CO_2$ incubator, cell monolayers were stained with 1 ml of a staining solution (3% crystal violet and 15% ethanol in $H_2O$). Plaques were counted and the percent neutralization was calculated relative to the number of plaques in the absence of antibody. Titers represent the reciprocal of the highest dilution resulting in a 50% reduction in the number of plaques. Mean neutralization titers for individual mice were plotted ±standard deviation.

Viral Challenges.

Five weeks after the boost, mice were anesthetized and weighed before intranasal administration with a plastic pipette tip containing 50 µl of PBS with $2 \times 10^6$ pfu of VACV strain IHD-J. This dose is three times the $LD_{50}$. Subsequently, mice were observed and weighed daily for 14 d. Moribund mice (>30% body weight) were euthanized.

Statistical Analysis:

The statistical significance of ELISAs and PRNTs were determined using the unpaired two-tailed Student's t test. Percent weight loss data comparisons between 4pox and 4pox (tPA-L1R) vaccinated mice were also examined by the unpaired two-tailed Student's t test at each day postinfection. Significance levels were set at a P value less than 0.05.

Full-Length tPA-L1R Interacts More Efficiently with Antibodies Against the Neutralizing Epitope Compared to tPA-L1R Lacking the Transmembrane Region.

An experiment was performed to determine if the presence of the predicted L1 transmembrane region and C-terminus was required for efficient expression of the important epitope bound by anti-L1 neutralizing antibodies.

Method: The tPA-L1R construct and a tPA-L1R construct lacking the transmembrane region (tPA-L1R 1-181) were flag tagged by cloning into the pCMVtag4 vector (Stratagene). COS-7 cells were transfected with tPA-L1R-FLAG and tPA-L1R181-FLAG and expression of the gene products were analyzed by Western blot using both an anti-FLAG antibody and an anti-L1 monoclonal antibody (MAb-10F5) that interacts with the potently neutralizing antibody epitope (Su, H and Golden, J W Virology 2007). The goal was to determine if the removal of the predicted L1 transmembrane region would affect the epitope bound by a neutralizing monoclonal antibody.

Results: As shown in FIG. 6, the anti-FLAG antibody bound to both the tPA-L1R-FLAG and tPA-L1R181-FLAG with similar intensity by Western blot. In contrast, MAb-10F5 interacted to a greater extent with full length L1 compared to L1 lacking the transmembrane region.

Conclusion: tPA-L1R-FLAG and the tPA-L1R181-FLAG, which lacks the transmembrane region, are expressed at similar levels in transfected cells. However, despite similar expression levels, tPA-L1R interacts with the neutralizing antibody Mab-10F5 to a much greater extent compared to the tPA-L1R18'-FLAG molecule. These findings were unexpected and indicate that the amino acids from 181 to the C-terminus of L1 are somehow involved in the efficient folding or accessibility of the epitope bound by MAb-10F5. Thus, a version of the tPA-L1R designed without the transmembrane region (e.g., designed to be secreted) would be less immunogenic than the full-length L1R construct.

The tPA-L1R Construct Overcomes a Previously Observed Interference Between Co-Delivered L1R and A33R DNA Vaccines.

We had previously found that when we mixed plasmids expressing L1R and A33R (e.g., precipitated on the same gold for gene gun delivery), there was a good response against A33 but essentially no response against L1 (no neutralizing antibody) (Hooper et al., 2000 Virology; [ref. 20]). In an attempt to overcome this interference, we tested the capacity of the tPA-L1R construct to elicit neutralizing antibodies when mixed with a plasmid expressing A33R.

Methods: DNA vaccination with gene-gun. Plasmid DNA was precipitated onto ~2-μM diameter gold beads at a concentration of 1 μg total DNA/1 mg of gold. This DNA-gold mixture was coated on the inner surface of irradiated Tefzel tubing and the tubing was cut into 0.5-in cartridges. Each cartridge contained ~0.25-0.5 μg of DNA coated on 0.5 mg of gold. All cartridges were quality controlled to ensure the presence of DNA. For vaccinations, the abdominal fur of BALB/c mice was shaved and DNA-coated gold was administered using a gene-gun (Powderjet delivery device, Powderject, INC) and compressed helium at 400 p.s.i. to non-overlapping sites. Mice were vaccinated with two cartridges containing individual genes or a 1:1 mixture of A33R and L1R or tPA-L1R at both the prime and boost. The boost was preformed three weeks after the priming vaccination. All mice were at least 7-9-weeks old at the start of vaccination.

Results: We tested the ability of the tPA-L1R construct to overcome this effect. Mice were vaccinated twice with A33R and unmodified L1R or tPA-L1R conjugated to the same gold carriers, L1R/A33R and tPA-L1R/A33R, respectively. Mice were also vaccinated with these genes delivered from separate cartridges (L1R+A33R and tPA-L1R+A33R). The antibody responses generated in vaccinated animals were then assessed by ELISA using purified L1 or A33 (FIG. 7A). Similar to previous reports, anti-L1 responses in most mice vaccinated with L1R/A33R were below detection, whereas the anti-A33 responses were over 2.5 logs. In contrast, tPA-L1R/A33R vaccinated animals had a high anti-L1 response. In this group, only half the animals had A33 responses that were above detection. When A33R and L1R or tPA-L1R plasmids were separated onto gold beads in different cartridges, antibody responses to both antigens were observed (FIG. 7A). PRNT50 titers correlated with level of anti-L1 antibodies (FIG. 7B). Thus, while L1R and A33R on the same gold carriers leads to poor anti-L1 responses, substituting tPA-L1R solves the problem allowing production of high anti-L1 titers in mixed plasmid formulations. Interestingly, the high-levels of anti-L1 antibody apparently had a slight adverse on the anti-A33 response because there was some reduction in the A33 response.

Conclusion: In an earlier study, we reported that mice vaccinated with A33R and L1R expressing plasmids conjugated to the same gold developed high anti-A33 but undetectable anti-L1 responses (i.e., no neutralizing antibodies) [ref. 20]. It was proposed that anti-A33 antibodies may have directed complement-mediated lysis of A33R (and L1R) expressing cells, thereby preventing a requisite boosting affect for the generation of an anti-L1 response. Subsequently it was determined that the interference was likely at the level of translation because cells co-transfected with both the L1R and A33R plasmids yielded decreased amounts of L1 and normal levels of A33, as measured by immunoprecipitation (Hooper, J. W., unpublished data). This conclusion is supported by our finding that vaccinating mice with A33R and tPA-L1R DNA conjugated to the same gold leads to high anti-L1 but decreased anti-A33 responses. Had anti-A33 antibodies been causing the lysis of A33/L1 expressing cells, one would expect to see some attenuation of antibody responses against L1 following the boost. However, in mice vaccinated with tPA-L1R/A33R, the anti-L1 responses increase two-fold and anti-A33 responses remain a bit lower. To reduce the number of cartridges required for each vaccination, the capacity to deliver two or more antigens in one cartridge would be ideal. Our findings here indicate that the substitution of tPA-L1R for unmodified L1R may allow expression of correctly folded in co-transfected cells.

REFERENCES

[ref. 1] Esposito J J, Sammons S A, Frace A M, Osborne J D, Olsen-Rasmussen M, Zhang M, et al. Genome sequence diversity and clues to the evolution of variola (smallpox) virus. Science 2006; 313(5788):807-12.

[ref. 2] Gubser C, Smith G L. The sequence of camelpox virus shows it is most closely related to variola virus, the cause of smallpox. J Gen Virol 2002 April; 83(Pt 4):855-72.

[ref. 3] Werden S J, McFadden G. The role of cell signaling in orthopoxvirus tropism: The case of the M-T5 host range protein of myxoma virus. Biochim Biophys Acta 2007 Aug. 14 (epub ahead of print).

[ref. 4] Lewis-Jones S. Zoonotic orthopoxvirus infections in humans. Curr Opin Infect Dis 2004 17:81-9.

[ref. 5] Parker S, Nuara A, Buller R M, Schultz D A. Human monkeypox: an emerging zoonotic disease. Future microbiology 2007; 2:17-34.

[ref. 6] Reed K D, Melski J W, Graham M B, Regnery R L, Sotir M J, Wegner M V, et al. The detection of monkeypox in humans in the Western Hemisphere. N Engl J Med 2004; 350(4):342-50.

[ref. 7] Lane J M, Goldstein J. Adverse events occurring after smallpox vaccination. Semin Pediatr Infect Dis 2003; 14(3):189-95.

[ref. 8] Wharton M, Strikas R A, Harpaz R, Rotz L D, Schwartz B, Casey C G, et al. Recommendations for using smallpox vaccine in a pre-event vaccination program. Supplemental recommendations of the Advisory Committee on Immunization Practices (ACIP) and the Healthcare Infection Control Practices Advisory Committee (HICPAC). MMWR Recomm Rep 2003; 52(RR-7): 1-16.

[ref. 9] Bray M. Pathogenesis and potential antiviral therapy of complications of smallpox vaccination. Antiviral Res 2003; 58:101-14.

[ref. 10] Kretzschmar M, Walling a J, Teunis P, Xing S, Mikolajczyk R. Frequency of adverse events after vaccination with different vaccinia strains. PLoS Med 2006; 3:e272.

[ref. 11] Earl P L, Americo J L, Wyatt L S, Eller L A, Whitbeck J C, Cohen G H, et al. Immunogenicity of a highly attenuated MVA smallpox vaccine and protection against monkeypox. Nature 2004; 428:182-5.

[ref. 12] McCurdy L H, Larkin B D, Martin J E, Graham B S. Modified vaccinia Ankara: potential as an alternative smallpox vaccine. Clin Infect Dis 2004; 38:1749-53.

[ref. 13] Coulibaly S, Bruhl P, Mayrhofer J, Schmid K, Gerencer M, Falkner F G. The nonreplicating smallpox candidate vaccines defective vaccinia Lister (dVV-L) and modified vaccinia Ankara (MVA) elicit robust long-term protection. Virology 2005; 341:91-101.

[ref. 14] Kidokoro M, Tashiro M, Shida H. Genetically stable and fully effective smallpox vaccine strain constructed from highly attenuated vaccinia LC16m8. Proc Natl Acad Sci USA 2005; 102:4152-7.

[ref. 15] Edghill-Smith Y, Bray M, Whitehouse C A, Miller D, Mucker E, Manischewitz J, et al. Smallpox vaccine does not protect macaques with AIDS from a lethal monkeypox virus challenge. J Infect Dis 2005; 191:372-81.

[ref. 16] Galmiche M C, Goenaga J, Wittek R, Rindisbacher L. Neutralizing and protective antibodies directed against vaccinia virus envelope antigens. Virology 1999; 254:71-80.

[ref. 17] Fang M, Cheng H, Dai Z, Bu Z, Sigal L J. Immunization with a single extracellular enveloped virus protein produced in bacteria provides partial protection from a lethal orthopoxvirus infection in a natural host. Virology 2006; 345:231-43.

[ref. 18] Davies D H, McCausland M M, Valdez C, Huynh D, Hernandez J E, Mu Y, et al. Vaccinia virus H3L envelope protein is a major target of neutralizing antibodies in humans and elicits protection against lethal challenge in mice. J Virol 2005; 79:11724-33.

[ref. 19] Sakhatskyy P, Wang S, Chou T H, Lu S. Immunogenicity and protection efficacy of monovalent and polyvalent orthopoxvirus vaccines that include the D8 antigen. Virology 2006; 355:164-74.

[ref. 20] Hooper J W, Custer D M, Schmaljohn C S, Schmaljohn A L. DNA vaccination with vaccinia virus L1R and A33R genes protects mice against a lethal orthopoxvirus challenge. Virology 2000; 266:329-39.

[ref. 21] Hooper J W, Custer D M, Thompson E. Four-gene-combination DNA vaccine protects mice against a lethal vaccinia virus challenge and elicits appropriate antibody responses in nonhuman primates. Virology 2003; 306:181-95.

[ref. 22] Hooper J W, Thompson E, Wilhelmsen C, Zimmerman M, Ichou M A, Steffen S E, et al. Smallpox DNA vaccine protects nonhuman primates against lethal monkeypox. J Virol 2004; 78:4433-43.

[ref. 23] Hooper J W, Golden J W, Ferro A M, King A D. Smallpox DNA vaccine delivered by novel skin electroporation device protects mice against intranasal orthopoxvirus challenge. Vaccine 2007; 25:1814-23.

[ref. 24] Fogg C, Lustig S, Whitbeck J C, Eisenberg R J, Cohen G H, Moss B. Protective immunity to vaccinia virus induced by vaccination with multiple recombinant outer membrane proteins of intracellular and extracellular virions. J Virol 2004; 78:10230-7.

[ref 25] Moss B. Orthopoxviruses and Their Replication. In: Knipe D M, Howley P M, editors. Fields Virology. 4th ed. Philadelphia: Lippencott, Williams and Wilkins, 2001: 1249-81.

[ref. 26] Franke C A, Wilson E M, Hruby D E. Use of a cell-free system to identify the vaccinia virus L1R gene product as the major late myristylated virion protein M25. J Virol 1990; 64:5988-96.

[ref. 27] Ravanello M P, Hruby D E. Conditional lethal expression of the vaccinia virus L1R myristylated protein reveals a role in virion assembly. J Virol 1994; 68:6401-10.

[ref 28] Ichihashi Y, Oie M. Neutralizing epitope on penetration protein of vaccinia virus. Virology 1996; 220:491-4.

[ref 29] Ichihashi Y, Takahashi T, Oie M. Identification of a vaccinia virus penetration protein. Virology 1994; 202: 834-43.

[ref 30] Wolffe E J, Vijaya S, Moss B. A myristylated membrane protein encoded by the vaccinia virus L1R open reading frame is the target of potent neutralizing monoclonal antibodies. Virology 1995; 211:53-63.

[ref. 31] Hooper J W, Schmaljohn A L, Schmaljohn C, inventors; The United States of America as represented by the Secretary of the Army, assignee. Prophylactic and Therapeutic Monoclonal Antibodies. U.S. Pat. No. 6,451,309. 2002.

[ref. 32] Su H P, Garman S C, Allison T J, Fogg C, Moss B, Garboczi D N. The 1.51-Angstrom structure of the orthopoxvirus L1 protein, a target of potent neutralizing antibodies. Proc Natl Acad Sci USA 2005; 102:4240-5.

[ref. 33] Senkevich T G, White C L, Koonin E V, Moss B. Complete pathway for protein disulfide bond formation encoded by orthopoxviruses. Proc Natl Acad Sci USA 2002; 99:6667-72.

[ref. 34] Su H P, Golden J W, Gittis A G, Hooper J W, Garboczi D N. Structural basis for the binding of the neutralizing antibody, 7D11, to the orthopoxvirus L1 protein. Virology 2007; 368:331-41.

[ref. 35] Edghill-Smith Y, Golding H, Manischewitz J, King L R, Scott D, Bray M, et al. Smallpox vaccine-induced antibodies are necessary and sufficient for protection against monkeypox virus. Nat Med 2005; 11:740-7.

[ref. 36] Panchanathan V, Chaudhri G, Karupiah G. Protective immunity against secondary orthopoxvirus infection is dependent on antibody but not on CD4 or CD8 T-cell function. J Virol 2006; 80(13):6333-8.

[ref. 37] Panchanathan V, Chaudhri G, Karupiah G. Correlates of protective immunity in orthopoxvirus infection: where does antibody stand? Immunol Cell Biol 2007 Oct. 9 (epub ahead of print).

[ref. 38] Schmaljohn C, Vanderzanden L, Bray M, Custer D, Meyer B, Li D, et al. Naked DNA vaccines expressing the prM and E genes of Russian spring summer encephalitis virus and Central European encephalitis virus protect mice from homologous and heterologous challenge. J Virol 1997; 71:9563-9.

[ref. 39] Rodriguez J F, Paez E, Esteban M. A 14,000-Mr envelope protein of vaccinia virus is involved in cell fusion and forms covalently linked trimers. J Virol 1987; 61:395-404.

[ref. 40] Feltquate D M, Heaney S, Webster R G, Robinson H L. Different T helper cell types and antibody isotypes generated by saline and gene gun DNA immunization. J Immunol 1997; 158:2278-84.

[ref. 41] Pulford D J, Gates A, Bridge S H, Robinson J H, Ulaeto D. Differential efficacy of vaccinia virus envelope proteins administered by DNA immunisation in protection of BALB/c mice from a lethal intranasal orthopoxvirus challenge. Vaccine 2004; 22:3358-66.

[ref. 42] Aldaz-Carroll L, Whitbeck J C, de Leon M P, Lou H, Pannell L K, Lebowitz J, et al. Physical and immunological characterization of a recombinant secreted form of the membrane protein encoded by the vaccinia virus L1R gene. Virology 2005 341:1588-97.

[ref. 43] Ashok M S, Rangarajan P N. Protective efficacy of a plasmid DNA encoding Japanese encephalitis virus envelope protein fused to tissue plasminogen activator signal sequences: studies in a murine intracerebral virus challenge model. Vaccine 2002; 20:1563-70.

[ref. 44] Rath A, Choudhury S, Batra D, Kapre S V, Rupprecht C E, Gupta S K. DNA vaccine for rabies: relevance of the trans-membrane domain of the glycoprotein in generating an antibody response. Virus Res 2005; 113:143-52.

[ref. 45] Costa S M, Paes M V, Barreto D F, Pinhao A T, Barth O M, Queiroz J L, et al. Protection against dengue type 2 virus induced in mice immunized with a DNA plasmid encoding the non-structural 1 (NS1) gene fused to the tissue plasminogen activator signal sequence. Vaccine 2006; 24:195-205.

[ref. 46] Delogu G, Li A, Repique C, Collins F, Morris S L. DNA vaccine combinations expressing either tissue plasminogen activator signal sequence fusion proteins or ubiquitin-conjugated antigens induce sustained protective immunity in a mouse model of pulmonary tuberculosis. Infect Immun 2002; 70:292-302.

[ref. 47] Li Z, Howard A, Kelley C, Delogu G, Collins F, Morris S. Immunogenicity of DNA vaccines expressing tuberculosis proteins fused to tissue plasminogen activator signal sequences. Infect Immun 1999; 67:4780-6.

[ref. 48] Wang S, Heilman D, Liu F, Giehl T, Joshi S, Huang X, et al. A DNA vaccine producing LcrV antigen in oligomers is effective in protecting mice from lethal mucosal challenge of plague. Vaccine 2004; 22:3348-57.

[ref. 49] Payne L G. Identification of the vaccinia hemagglutinin polypeptide from a cell system yielding large amounts of extracellular enveloped virus. J Virol 1979; 31:147-55.

[ref. 50] Fogg C N, Americo J L, Lustig S, Huggins J W, Smith S K, Damon I, et al. Adjuvant-enhanced antibody responses to recombinant proteins correlates with protection of mice and monkeys to orthopoxvirus challenges. Vaccine 2007; 25:2787-99.

[ref. 51] Heraud J M, Edghill-Smith Y, Ayala V, Kalisz I, Parrino J, Kalyanaraman V S, et al. Subunit recombinant vaccine protects against monkeypox. J Immunol 2006; 177:2552-64.

The contents of all references cited herein are incorporated by reference in their entirety.

The contents of U.S. Pat. No. 6,562,376 and U.S. Pat. No. 6,451,309 are incorporated by reference in their entirety.

```
SEQ ID NO: 1 -- tPT L1R 7079 sequence
CGTCTGCTGAGACTAACAGACTGTTCCTTTCCATGGGTCTTTTCTGCAG

TCACCGTCCAAGCTTGCAATCATGGATGCAATGAAGAGAGGGCTCT

GCTGTGTGCTGCTGCTGTGTGGAGCAGTCTTCGTTTCGGCTAGCAT

GGGTGCCGCAGCAAGCATACAGACGACGGTGAATACACTCAGCGAAC

GTATCTCGTCTAAATTAGAACAAGAAGCGAACGCTAGTGCTCAAACAA

AATGTGATATAGAAATCGGAAATTTTTATATCCGACAAAACCATGGAT

GTAACCTCACTGTTAAAAATATGTGCTCTGCGGACGCGGATGCTCAGT

TGGATGCTGTGTTATCAGCCGCTACAGAAACATATAGTGGATTAACAC

CGGAACAAAAAGCATACGTACCAGCTATGTTTACTGCTGCGTTAAACA
```

```
TTCAGACAAGTGTAAACACTGTTGTTAGAGATTTTGAAAATTATGTGA

AACAAACTTGTAATTCTAGCGCGGTCGTCGATAACAAATTAAAGATAC

AAAACGTAATCATAGATGAATGTTACGGAGCCCCAGGATCTCCAACAA

ATTTGGAATTTATTAATACAGGATCTAGCAAAGGAAATTGTGCCATTA

AGGCGTTGATGCAATTGACTACTAAGGCCACTACTCAAATAGCACCTA

AACAAGTTGCTGGTACAGGAGTTCAGTTTTATATGATTGTTATCGGTGT

TATAATATTGGCAGCGTTGTTTATGTACTATGCCAAGCGTATGCTGTTC

ACATCCACCAATGATAAAATCAAACTTATTTTAGCCAATAAGGAAAAC

GTCCATTGGACTACTTACATGGACACATTCTTTAGAACTTCTCCGATGG

GTTATTGCTACCACGGATATGCAAACTGAAGATCTACGTATGATCAGCT
```

CGACTGTGCTTCTAGTTGCAGCCATCTGTTGTTTGCCCCTCCCCCGTGC

TCTGGACCTGAAGGTGCCACTCCCCACTGTCTTTCTATAATGAGATGGC

ATCGCATTGCCTGGATAGGTCATCTATCCAGGCTTGTTGGCAGGACCA

AGGGAGATGGCGACATTCAGCATGCTGGGATCG

L1R gene is underlined

NheI restriction site is the first italics just prior
to the underlined L1R gene, and is GCTAGC BglII restriction site is the second italics just after
the underlined L1R gene, and is AGATCT TPA signal sequence is shown in bold Other sequence is from the pWRG7079 vector (this vector
contained the TPA signal sequence)

L1R was cloned into the NheI and BglII sites of pWRG7079
making the gene in-frame with the TPA signal sequence.

SEQ ID NO: 2 -- pWRG7079
GGGGGGGGGGGCGCTGAGGTCTGCCTCGTGAAGAAGGTGTTGCTGA

CTCATACCAGGCCTGAATCGCCCCATCATCCAGCCAGAAAGTGAGGGA

GCCACGGTTGATGAGAGCTTTGTTGTAGGTGGACCAGTTGGTGATTTT

GAACTTTTGCTTTGCCACGGAACGGTCTGCGTTGTCGGGAAGATGCGT

GATCTGATCCTTCAACTCAGCAAAAGTTCGATTTATTCAACAAAGCCG

CCGTCCCGTCAAGTCAGCGTAATGCTCTGCCAGTGTTACAACCAATTA

ACCAATTCTGATTAGAAAAACTCATCGAGCATCAAATGAAACTGCAAT

TTATTCATATCAGGATTATCAATACCATATTTTTGAAAAAGCCGTTTCT

GTAATGAAGGAGAAAACTCACCGAGGCAGTTCCATAGGATGGCAAGA

TCCTGGTATCGGTCTGCGATTCCGACTCGTCCAACATCAATACAACCTA

TTAATTTCCCCTCGTCAAAAATAAGGTTATCAAGTGAGAAATCACCAT

GAGTGCGACTGAATCCGGTGAGAATGGCAAAAGCTTATGCATTTCTTT

CCAGACTTGTTCAACAGGCCAGCCATTACGCTCGTCATCAAAATCACT

CGCATCAACCAAACCGTTATTCATTCGTGATTGCGCCTGAGCGAGACG

AAATACGCGATCGCTGTTAAAAGGACAATTACAAACAGGAATCGAAT

GCAACCGGCGCAGGAACACTGCCAGCGCATCAACAATATTTTCACCTG

AATCAGGATATTCTTCTAATACCTGGAATGCTGTTTTCCCGGGGATCGC

AGTGGTGAGTAACCATGCATCATCAGGAGTACGGATAAAATGCTTGAT

-continued

```
GGTCGGAAGAGGCATAAATTCCGTCAGCCAGTTTAGTCTGACCATCTC
ATCTGTAACATCATTGGCAACGCTACCTTTGCCATGTTTCAGAAACA
ACTCTGGCGCATCGGGCTTCCCATACAATCGATAGATTGTCGCACCTG
ATTGCCCGACATTATCGCGAGCCCATTTATACCCATATAAATCAGCATC
CATGTTGGAATTTAATCGCGGCCTCGAGCAAGACGTTTCCCGTTGAAT
ATGGCTCATAACACCCCTTGTATTACTGTTTATGTAAGCAGACAGTTTT
ATTGTTCATGATGATATATTTTTATCTTGTGCAATGTAACATCAGAGAT
TTTGAGACACAACGTGGCTTTCCCCCCCCCCCCGGCATGCCTGCAGGT
CGACATAAATCAATATTGGCTATTGGCCATTGCATACGTTGTATCTATA
TCATAATATGTACATTTATATTGGCTCATGTCCAATATGACCGCCATGT
TGACATTGATTATTGACTAGTTATTAATAGTAATCAATTACGGGGTCAT
TAGTTCATAGCCCATATATGGAGTTCCGCGTTACATAACTTACGGTAA
ATGGCCCGCCTCGTGACCGCCCAACGACCCCCGCCCATTGACGTCAAT
AATGACGTATGTTCCCATAGTAACGCCAATAGGGACTTTCCATTGACG
TCAATGGGTGGAGTATTTACGGTAAACTGCCCACTTGGCAGTACATCA
AGTGTATCATATGCCAAGTCCGGCCCCCTATTGACGTCAATGACGGTA
AATGGCCCGCCTGGCATTATGCCCAGTACATGACCTTACGGGACTTTC
CTACTTGGCAGTACATCTACGTATTAGTCATCGCTATTACCATGGTGAT
GCGGTTTTGGCAGTAGACCAATGGGCGTGGATAGCGGTTTGACTCACG
GGGATTTCCAAGTCTCCACCCCATTGACGTCAATGGGAGTTTGTTTTGG
CACCAAAATCAACGGGACTTTCCAAAATGTCGTAATAACCCCGCCCCG
TTGACGCAAATGGGCGGTAGGCGTGTACGGTGGGAGGTCTATATAAGC
AGAGCTCGTTTAGTGAACCGTCAGATCGCCTGGAGACGCCATCCACGC
TGTTTTGACCTCCATAGAAGACACCGGGACCGATCCAGCCTCCGCGGC
CGGGAACGGTGCATTGGAACGCGGATTCCCCGTGCCAAGAGTGACGTA
AGTACCGCCTATAGACTCTATAGGCACACCCCTTTGGCTCTTATGCATG
CTATACTGTTTTTGGCTTGGGGCCTATACACCCCCGCTCCTTATGCTAT
AGGTGATGGTATAGCTTAGCCTATAGGTGTGGGTTATTGACCATTATTG
ACCACTCCCTATTGGTGACGATACTTTCCATTACTAATCCATAACATG
GCTCTTTGCCACAACTATCTCTATTGGCTATATGCCAATACTCTGTCCT
TCAGAGACTGACACGGACTCTGTATTTTTACAGGATGGGGTCCCATTT
ATTATTTACAAATTCACATATACAACAACGCCGTCCCCCGTGCCCGCA
GTTTTTATTAAACATAGCGTGGGATCTCCACGCGAATCTCGGGTACGT
GTTCCGGACATGGGCTCTTCTCCGGTAGCGGCGGAGCTTCCACATCCG
AGCCCTGGTCCCATGCCTCCAGCGGCTCATGGTCGCTCGGCAGCTCCTT
GCTCCTAACAGTGGAGGCCAGACTTAGGCACAGCACAATGCCCACCAC
CACCAGTGTGCCGCACAAGGCCGTGGCGGTAGGGTATGTGTCTGAAAA
TGAGCTCGGAGATTGGGCTCGCACCGTGACGCAGATGGAAGACTTAAG
GCAGCGGCAGAAGAAGATGCAGGCAGCTGAGTTGTTGTATTCTGATAA
GAGTCAGAGGTAACTCCCGTTGCGGTGCTGTTAACGGTGGAGGGCAGT
GTAGTCTGAGCAGTACTCGTTGCTGCCGCGCGCGCCACCAGACATAAT
```

```
AGCTGACAGACTAACAGACTGTTCCTTTCCATGGGTCTTTTCTGCAGTC
ACCGTCCAAGCTTGCAATCATGGATGCAATGAAGAGAGGGCTCTGCTG
TGTGCTGCTGCTGTGTGGAGCAGTCTTCGTTTCGGCTAGCCCCGGGTG
ATAAGGATCCTCGCAATCCCTAGGAGGATTAGGCAAGGGCTTGAGCTC
ACGCTCTTGTGAGGGACAGAAATACAATCAGGGGCAGTATATGAATAC
TCCATGGAGAAACCCAGATCTACGTATGATCAGCCTCGACTGTGCCTT
CTAGTTGCCAGCCATCTGTTGTTTGCCCCTCCCCCGTGCCTTCCTTGAC
CCTGGAAGGTGCCACTCCCACTGTCCTTTCCTAATAAAATGAGGAAAT
TGCATCGCATTGTCTGAGTAGGTGTCATTCTATTCTGGGGGTGGGGTG
GGGCAGGACAGCAAGGGGGAGGATTGGGAAGACAATAGCAGGCATGC
TGGGGATGCGGTGGGCTCTATGGCTTCTGAGGCGGAAAGAACCAGCTG
GGGCTCGACAGCTCGACTCTAGAATTGCTTCCTCGCTCACTGACTCGCT
GCGCTCGGTCGTTCGGCTGCGGCGAGCGGTATCAGCTCACTCAAAGGC
GGTAATACGGTTATCCACAGAATCAGGGGATAACGCAGGAAAGAACA
TGTGAGCAAAAGGCCAGCAAAAGGCCAGGAACCGTAAAAAGGCCGCG
TTGCTGGCGTTTTTCCATAGGCTCCGCCCCCCTGACGAGCATCACAAAA
ATCGACGCTCAAGTCAGAGGTGGCGAAACCCGACAGGACTATAAAGA
TACCAGGCGTTTCCCCCTGGAAGCTCCCTCGTGCGCTCTCCTGTTCCGA
CCCTGCCGCTTACCGGATACCTGTCCGCCTTTCTCCCTTCGGGAAGCGT
GGCGCTTTCTCAATGCTCACGCTGTAGGTATCTCAGTTCGGTGTAGGTC
GTTCGCTCCAAGCTGGGCTGTGTGCACGAACCCCCCGTTCAGCCCGAC
CGCTGCGCCTTATCCGGTAACTATCGTCTTGAGTCCAACCCGGTAAGA
CACGACTTATCGCCACTGGCAGCAGCCACTGGTAACAGGATTAGCAGA
GCGAGGTATGTAGGCGGTGCTACAGAGTTCTTGAAGTGGTGGCCTAAC
TACGGCTACACTAGAAGGACAGTATTTGGTATCTGCGCTCTGCTGAAG
CCAGTTACCTTCGGAAAAAGAGTTGGTAGCTCTTGATCCGGCAAACAA
ACCACCGCTGGTAGCGGTGGTTTTTTTGTTTGCAAGCAGCAGATTACGC
GCAGAAAAAAAGGATCTCAAGAAGATCCTTTGATCTTTTCTACGGGGT
CTGACGCTCAGTGGAACGAAAACTCACGTTAAGGGATTTTGGTCATGA
GATTATCAAAAAGGATCTTCACCTAGATCCTTTTAAATTAAAAATGAA
GTTTTAAATCAATCTAAAGTATATATGAGTAAACTTGGTCTGACAGTTA
CCAATGCTTAATCAGTGAGGCACCTATCTCAGCGATCTGTCTATTTCGT
TCATCCATAGTTGCCTGACTC

Codon optimized L1R

SEQ ID NO: 3 DNA sequence

SEQ ID NO: 4 amino acid sequence optimized for Homo sapiens

NarI
KasI
KpnI  NcoI  HaeII
GGGCGAATTGGGTACCGCCACCATGGGCGCCGCCGCCAGCATCCAGA
CCACCGTGAACAC
1 ---------+---------+---------+---------+---------+---------+
```

```
                 CCCGCTTAACCCATGGCGGTGGTACCCGCGGCGGCGGTCGTAGGTCTG
                 GTGGCACTTGTG
                  M  G  A  A  A  S  I  Q  T  T  V  N  T

HaeII
                 CCTGAGCGAGCGGATCAGCAGCAAGCTGGAGCAGGAGGCCAACGCCA
                 GCGCCCAGACCAA
              61 ---------+---------+---------+---------+---------+---------+

GGACTCGCTCGCCTAGTCGTCGTTCGACCTCGTCCTCCGGTTGCGGTCG
                 CGGGTCTGGTT
                  L  S  E  R  I  S  S  K  L  E  Q  E  A  N  A  S  A  Q  T  K

GTGTGACATCGAGATCGGCAACTTCTACATCCGGCAGAACCACGGCTG
                 TAACCTGACCGT
             121 ---------+---------+---------+---------+---------+---------+

CACACTGTAGCTCTAGCCGTTGAAGATGTAGGCCGTCTTGGTGCCGAC
                 ATTGGACTGGCA
                  C  D  I  E  I  G  N  F  Y  I  R  Q  N  H  G  C  N  L  T  V

HaeII PvuII
                 GAAGAACATGTGTAGCGCCGATGCCGACGCCCAGCTGGACGCCGTGCT
                 GTCCGCCGCCAC
             181 ---------+---------+---------+---------+---------+---------+

CTTCTTGTACACATCGCGGCTACGGCTGCGGGTCGACCTGCGGCACGA
                 CAGGCGGCGGTG
                  K  N  M  C  S  A  D  A  D  A  Q  L  D  A  V  L  S  A  A
                  T

BsaI
                 CGAGACCTACAGCGGCCTGACCCCCGAGCAGAAAGCCTACGTGCCCG
                 CCATGTTCACAGC
             241 ---------+---------+---------+---------+---------+---------+

GCTCTGGATGTCGCCGGACTGGGGGCTCGTCTTTCGGATGCACGGGCG
                 GTACAAGTGTCG
                  E  T  Y  S  G  L  T  P  E  Q  K  A  Y  V  P  A  M  F  T
                  A

CGCCCTGAACATCCAGACAAGCGTGAATACCGTTGTGAGGGACTTCGA
                 GAACTACGTGAA
             301 ---------+---------+---------+---------+---------+---------+

GCGGGACTTGTAGGTCTGTTCGCACTTATGGCAACACTCCCTGAAGCT
                 CTTGATGCACTT
                  A  L  N  I  Q  T  S  V  N  T  V  V  R  D  F  E  N  Y  V
                  K

HaeII BclI
                 GCAGACCTGTAACAGCAGCGCCGTGGTGGACAACAAGCTGAAGATCC
                 AGAACGTGATCAT
             361 ---------+---------+---------+---------+---------+---------+

CGTCTGGACATTGTCGTCGCGGCACCACCTGTTGTTCGACTTCTAGGTC
                 TTGCACTAGTA
                  Q  T  C  N  S  S  A  V  V  D  N  K  L  K  I  Q  N  V  I  I

BstNI BstXI
                 CGACGAGTGCTACGGAGCCCCTGGCAGCCCCACCAATCTGGAGTTCAT
                 CAACACCGGCAG
             421 ---------+---------+---------+---------+---------+---------+

GCTGCTCACGATGCCTCGGGGACCGTCGGGGTGGTTAGACCTCAAGTA
                 GTTGTGGCCGTC
                  D  E  C  Y  G  A  P  G  S  P  T  N  L  E  F  I  N  T  G  S

PvuII
                 CAGCAAGGGCAACTGTGCCATCAAGGCCCTGATGCAGCTGACCACCA
                 AGGCCACCACCCA
             481 ---------+---------+---------+---------+---------+---------+

GTCGTTCCCGTTGACACGGTAGTTCCGGGACTACGTCGACTGGTGGTTC
                 CGGTGGTGGGT
                  S  K  G  N  C  A  I  K  A  L  M  Q  L  T  T  K  A  T  T
```

```
                      Q
                      1

BstXI
BspMI BclI
GATCGCCCCCAAGCAGGTGGCCGGCACCGGCGTGCAGTTCTACATGAT
CGTGATCGGCGT
541 ---------+---------+---------+---------+---------+---------+

CTAGCGGGGGTTCGTCCACCGGCCGTGGCCGCACGTCAAGATGTACTA
GCACTAGCCGCA
    I  A  P  K  Q  V  A  G  T  G  V  Q  F  Y  M  I  V  I  G
    V

BstNI
GATCATCCTGGCCGCCCTGTTCATGTACTACGCCAAGCGGATGCTGTTC
ACCAGCACCAA
601 ---------+---------+---------+---------+---------+---------+

CTAGTAGGACCGGCGGGACAAGTACATGATGCGGTTCGCCTACGACAA
GTGGTCGTGGTT
    I  I  L  A  A  L  F  M  Y  Y  A  K  R  M  L  F  T  S  T  N

BstNI BstXI
CGACAAGATCAAGCTGATCCTGGCCAACAAGGAAAACGTGCACTGGA
CCACCTACATGGA
661 ---------+---------+---------+---------+---------+---------+

GCTGTTCTAGTTCGACTAGGACCGGTTGTTCCTTTTGCACGTGACCTGG
TGGATGTACCT
    D  K  I  K  L  I  L  A  N  K  E  N  V  H  W  T  T  Y  M
    D

BstXI NcoI SacI
CACCTTTTTCCGGACCAGCCCCATGGTGATCGCCACCACCGACATGCA
GAACTGATGAGA
721 ---------+---------+---------+---------+---------+---------+

GTGGAAAAAGGCCTGGTCGGGGTACCACTAGCGGTGGTGGCTGTACGT
CTTGACTACTCT
    T  F  F  R  T  S  P  M  V  I  A  T  T  D  M  Q  N  *  *
GCTCCAGCTTTTGTTCCC

781---------+--------
CGAGGTCGAAAACAAGGG
2
```

---

What is claimed is:

1. A DNA immunogenic composition comprising SEQ ID NO:1, wherein SEQ ID NO:1 comprises
   a modified full-length poxvirus L1R gene encoding a modified poxvirus L1R antigen which includes a transmembrane domain, and
   a polynucleotide sequence encoding an endoplasmic reticulum-targeting sequence tissue plasminogen leader sequence (tPA) fused to the N terminus of the polynucleotide sequence of the modified poxvirus L1R antigen, encoded by the full-length poxvirus L1R gene,
   wherein the DNA immunogenic composition is capable of generating neutralizing antibodies specific for the modified poxvirus L1R antigen.

2. The DNA immunogenic composition of claim 1, wherein when administered to a mammal or avian species expresses the modified poxvirus L1R antigen that is not secreted and that has the property of proper folding.

3. The DNA immunogenic composition of claim 1, which further includes an adjuvant.

4. The DNA immunogenic composition of claim 1, wherein the full-length L1R gene expresses the modified poxvirus L1R antigen that has the property of proper folding and contains the epitopes recognized by the monoclonal antibodies MAb-10F5 and/or MAb-7D11.

5. The DNA immunogenic composition of claim 1, which is present in an amount sufficient to elicit an immune response in an animal susceptible to a poxvirus.

6. The DNA immunogenic composition of claim 1, wherein the composition is capable of generating neutralizing antibodies specific for the L1R antigen following two doses.

7. The immunogenic composition of claim 1, wherein the neutralizing antibodies bind the loop regions of L1R peptide held together by the disulfide bond between cysteine at amino acid position 34 and cysteine at amino acid position 57, corresponding to the L1R sequence in the vaccinia virus.

8. The DNA immunogenic composition of claim 1, wherein the DNA immunogenic composition when expressed in vivo produces a modified poxvirus L1R antigen which forms disulfide bonds utilizing the disulfide bond formation components of the endoplasmic reticulum of a cell transfected therewith.

9. The immunogenic composition of claim 1, which is pWRG/TPA-L1 Rco.

* * * * *

SEQUENCE LISTING

<160> NUMBER OF SEQ ID NOS: 8

<210> SEQ ID NO 1
<211> LENGTH: 1091
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
cgtctgctga gactaacaga ctgttccttt ccatgggtct tttctgcagt caccgtccaa      60
gcttgcaatc atggatgcaa tgaagagagg gctctgctgt gtgctgctgc tgtgtggagc     120
agtcttcgtt tcggctagca tgggtgccgc agcaagcata cagacgacgg tgaatacact     180
cagcgaacgt atctcgtcta aattagaaca agaagcgaac gctagtgctc aaacaaaatg     240
tgatatagaa atcggaaatt tttatatccg acaaaaccat ggatgtaacc tcactgttaa     300
aaatatgtgc tctgcggacg cggatgctca gttggatgct gtgttatcag ccgctacaga     360
aacatatagt ggattaacac cggaacaaaa agcatacgta ccagctatgt ttactgctgc     420

-continued

| | |
|---|---|
| gttaaacatt cagacaagtg taaacactgt tgttagagat tttgaaaatt atgtgaaaca | 480 |
| aacttgtaat tctagcgcgg tcgtcgataa caaattaaag atacaaaacg taatcataga | 540 |
| tgaatgttac ggagccccag gatctccaac aaatttggaa tttattaata caggatctag | 600 |
| caaaggaaat tgtgccatta aggcgttgat gcaattgact actaaggcca ctactcaaat | 660 |
| agcacctaaa caagttgctg gtacaggagt tcagttttat atgattgtta tcggtgttat | 720 |
| aatattggca gcgttgttta tgtactatgc caagcgtatg ctgttcacat ccaccaatga | 780 |
| taaaatcaaa cttatttttag ccaataagga aaacgtccat tggactactt acatggacac | 840 |
| attcttttaga acttctccga tgggttattg ctaccacgga tatgcaaact gaagatctac | 900 |
| gtatgatcag ctcgactgtg cttctagttg cagccatctg ttgtttgccc ctcccccgtg | 960 |
| ctctggacct gaaggtgcca ctccccactg tctttctata atgagatggc atcgcattgc | 1020 |
| ctggataggt catctatcca ggcttgttgg caggaccaag ggagatggcg acattcagca | 1080 |
| tgctgggatc g | 1091 |

<210> SEQ ID NO 2
<211> LENGTH: 4409
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

| | |
|---|---|
| gggggggggg ggcgctgagg tctgcctcgt gaagaaggtg ttgctgactc ataccaggcc | 60 |
| tgaatcgccc catcatccag ccagaaagtg agggagccac ggttgatgag agctttgttg | 120 |
| taggtggacc agttggtgat tttgaacttt tgctttgcca cggaacggtc tgcgttgtcg | 180 |
| ggaagatgcg tgatctgatc cttcaactca gcaaaagttc gatttattca acaaagccgc | 240 |
| cgtcccgtca agtcagcgta atgctctgcc agtgttacaa ccaattaacc aattctgatt | 300 |
| agaaaaactc atcgagcatc aaatgaaact gcaatttatt catatcagga ttatcaatac | 360 |
| catattttg aaaagccgt ttctgtaatg aaggagaaaa ctcaccgagg cagttccata | 420 |
| ggatggcaag atcctggtat cggtctgcga ttccgactcg tccaacatca atacaaccta | 480 |
| ttaatttccc ctcgtcaaaa ataaggttat caagtgagaa atcaccatga gtgcgactga | 540 |
| atccggtgag aatggcaaaa gcttatgcat ttctttccag acttgttcaa caggccagcc | 600 |
| attacgctcg tcatcaaaat cactcgcatc aaccaaaccg ttattcattc gtgattgcgc | 660 |
| ctgagcgaga cgaaatacgc gatcgctgtt aaaaggacaa ttacaaacag gaatcgaatg | 720 |
| caaccggcgc aggaacactg ccagcgcatc aacaatattt tcacctgaat caggatattc | 780 |
| ttctaatacc tggaatgctg ttttcccggg gatcgcagtg gtgagtaacc atgcatcatc | 840 |
| aggagtacgg ataaaatgct tgatggtcgg aagaggcata aattccgtca gccagtttag | 900 |
| tctgaccatc tcatctgtaa catcattggc aacgctacct ttgccatgtt tcagaaacaa | 960 |
| ctctggcgca tcgggcttcc catacaatcg atagattgtc gcacctgatt gcccgacatt | 1020 |
| atcgcgagcc catttatacc catataaatc agcatccatg ttggaattta atcgcggcct | 1080 |
| cgagcaagac gtttcccgtt gaatatggct cataacaccc cttgtattac tgtttatgta | 1140 |
| agcagacagt tttattgttc atgatgatat ttttttatct tgtgcaatgt aacatcagag | 1200 |
| attttgagac acaacgtggc tttcccccccc ccccggcat gcctgcaggt cgacataaat | 1260 |
| caatattggc tattggccat tgcatacgtt gtatctatat cataatatgt acatttatat | 1320 |
| tggctcatgt ccaatatgac cgccatgttg acattgatta ttgactagtt attaatagta | 1380 |

```
atcaattacg gggtcattag ttcatagccc atatatggag ttccgcgtta cataacttac    1440
ggtaaatggc ccgcctcgtg accgcccaac gaccccgcc cattgacgtc aataatgacg     1500
tatgttccca tagtaacgcc aatagggact ttccattgac gtcaatgggt ggagtattta    1560
cggtaaactg cccacttggc agtacatcaa gtgtatcata tgccaagtcc ggcccctat    1620 tgacgtcaat gacggtaaat ggcccgcctg gcattatgcc cagtacatga ccttacggga    1680
ctttcctact tggcagtaca tctacgtatt agtcatcgct attaccatgg tgatgcggtt    1740
ttggcagtac accaatgggc gtggatagcg gtttgactca cggggatttc caagtctcca    1800
ccccattgac gtcaatggga gtttgttttg gcaccaaaat caacgggact ttccaaaatg    1860
tcgtaataac cccgccccgt tgacgcaaat gggcggtagg cgtgtacggt gggaggtcta    1920
tataagcaga gctcgtttag tgaaccgtca gatcgcctgg agacgccatc cacgctgttt    1980
tgacctccat agaagacacc gggaccgatc cagcctccgc ggccgggaac ggtgcattgg    2040
aacgcggatt ccccgtgcca agagtgacgt aagtaccgcc tatagactct ataggcacac    2100 cccctttggct cttatgcatg ctatactgtt tttggcttgg ggcctataca ccccgctcc    2160 ttatgctata ggtgatggta tagcttagcc tataggtgtg ggttattgac cattattgac    2220
cactccccta ttggtgacga tactttccat tactaatcca taacatggct ctttgccaca    2280
actatctcta ttggctatat gccaatactc tgtccttcag agactgacac ggactctgta    2340
tttttacagg atggggtccc atttattatt tacaaattca catatacaac aacgccgtcc    2400
cccgtgcccg cagttttat taaacatagc gtgggatctc cacgcgaatc tcgggtacgt    2460
gttccggaca tgggctcttc tccggtagcg gcggagcttc cacatccgag ccctggtccc    2520
atgcctccag cggctcatgg tcgctcggca gctccttgct cctaacagtg gaggccagac    2580
ttaggcacag cacaatgccc accaccacca gtgtgccgca caaggccgtg gcggtagggt    2640
atgtgtctga aaatgagctc ggagattggg ctcgcaccgt gacgcagatg gaagacttaa    2700
ggcagcggca gaagaagatg caggcagctg agttgttgta ttctgataag agtcagaggt    2760
aactcccgtt gcggtgctgt taacggtgga gggcagtgta gtctgagcag tactcgttgc    2820
tgccgcgcgc gccaccagac ataatagctg acagactaac agactgttcc tttccatggg    2880
tcttttctgc agtcaccgtc caagcttgca atcatggatg caatgaagag agggctctgc    2940
tgtgtgctgc tgctgtgtgg agcagtcttc gtttcggcta gccccgggtg ataaggatcc    3000
tcgcaatccc taggaggatt aggcaagggc ttgagctcac gctcttgtga gggacagaaa    3060
tacaatcagg ggcagtatat gaatactcca tggagaaacc cagatctacg tatgatcagc    3120
ctcgactgtg ccttctagtt gccagccatc tgttgtttgc cctcccccg tgccttcctt     3180 gaccctggaa ggtgccactc ccactgtcct ttcctaataa aatgaggaaa ttgcatcgca    3240
ttgtctgagt aggtgtcatt ctattctggg ggtgggtg gggcaggaca gcaaggggga     3300
ggattgggaa gacaatagca ggcatgctgg ggatgcggtg gctctatgg cttctgaggc    3360 ggaaagaacc agctgggct cgacagctcg actctagaat tgcttcctcg ctcactgact     3420
cgctgcgctc ggtcgttcgg ctgcggcgag cggtatcagc tcactcaaag gcggtaatac    3480
ggttatccac agaatcaggg gataacgcag aaagaacat gtgagcaaaa ggccagcaaa     3540
aggccaggaa ccgtaaaaag gccgcgttgc tggcgttttt ccataggctc cgccccctg    3600 acgagcatca aaaaatcga cgctcaagtc agaggtggcg aaacccgaca ggactataaa    3660
gataccaggc gtttccccct ggaagctccc tcgtgcgctc tcctgttccg acctgccgc    3720 ttaccggata cctgtccgcc tttctccctt cgggaagcgt ggcgctttct caatgctcac    3780
```

```
gctgtaggta tctcagttcg gtgtaggtcg ttcgctccaa gctgggctgt gtgcacgaac    3840 ccccccgttca gcccgaccgc tgcgccttat ccggtaacta tcgtcttgag tccaacccgg    3900
taagacacga cttatcgcca ctggcagcag ccactggtaa caggattagc agagcgaggt    3960
atgtaggcgg tgctacagag ttcttgaagt ggtggcctaa ctacggctac actagaagga    4020
cagtatttgg tatctgcgct ctgctgaagc cagttacctt cggaaaaaga gttggtagct    4080
cttgatccgg caaacaaacc accgctggta gcggtggttt ttttgtttgc aagcagcaga    4140
ttacgcgcag aaaaaaagga tctcaagaag atcctttgat cttttctacg ggtctgacg    4200 ctcagtggaa cgaaaactca cgttaaggga ttttggtcat gagattatca aaaaggatct    4260
tcacctagat ccttttaaat taaaaatgaa gttttaaatc aatctaaagt atatatgagt    4320
aaacttggtc tgacagttac caatgcttaa tcagtgaggc acctatctca gcgatctgtc    4380
tatttcgttc atccatagtt gcctgactc                                     4409
```

<210> SEQ ID NO 3
<211> LENGTH: 798
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (23)..(772)

<400> SEQUENCE: 3

```
gggcgaattg ggtaccgcca cc atg ggc gcc gcc gcc agc atc cag acc acc        52
                         Met Gly Ala Ala Ala Ser Ile Gln Thr Thr
                         1               5                    10 gtg aac acc ctg agc gag cgg atc agc agc aag ctg gag cag gag gcc       100
Val Asn Thr Leu Ser Glu Arg Ile Ser Ser Lys Leu Glu Gln Glu Ala
                 15                  20                  25 aac gcc agc gcc cag acc aag tgt gac atc gag atc ggc aac ttc tac       148
Asn Ala Ser Ala Gln Thr Lys Cys Asp Ile Glu Ile Gly Asn Phe Tyr
         30                  35                  40 atc cgg cag aac cac ggc tgt aac ctg acc gtg aag aac atg tgt agc       196
Ile Arg Gln Asn His Gly Cys Asn Leu Thr Val Lys Asn Met Cys Ser
     45                  50                  55 gcc gat gcc gac gcc cag ctg gac gcc gtg ctg tcc gcc gcc acc gag       244
Ala Asp Ala Asp Ala Gln Leu Asp Ala Val Leu Ser Ala Ala Thr Glu
 60                  65                  70 acc tac agc ggc ctg acc ccc gag cag aaa gcc tac gtg ccc gcc atg       292
Thr Tyr Ser Gly Leu Thr Pro Glu Gln Lys Ala Tyr Val Pro Ala Met
 75                  80                  85                  90 ttc aca gcc gcc ctg aac atc cag aca agc gtg aat acc gtt gtg agg       340
Phe Thr Ala Ala Leu Asn Ile Gln Thr Ser Val Asn Thr Val Val Arg
                 95                 100                 105 gac ttc gag aac tac gtg aag cag acc tgt aac agc agc gcc gtg gtg       388
Asp Phe Glu Asn Tyr Val Lys Gln Thr Cys Asn Ser Ser Ala Val Val
             110                 115                 120 gac aac aag ctg aag atc cag aac gtg atc atc gac gag tgc tac gga       436
Asp Asn Lys Leu Lys Ile Gln Asn Val Ile Ile Asp Glu Cys Tyr Gly
         125                 130                 135 gcc cct ggc agc ccc acc aat ctg gag ttc atc aac acc ggc agc agc       484
Ala Pro Gly Ser Pro Thr Asn Leu Glu Phe Ile Asn Thr Gly Ser Ser
     140                 145                 150 aag ggc aac tgt gcc atc aag gcc ctg atg cag ctg acc acc aag gcc       532
Lys Gly Asn Cys Ala Ile Lys Ala Leu Met Gln Leu Thr Thr Lys Ala
155                 160                 165                 170
```

```
acc acc cag atc gcc ccc aag cag gtg gcc ggc acc ggc gtg cag ttc      580
Thr Thr Gln Ile Ala Pro Lys Gln Val Ala Gly Thr Gly Val Gln Phe
            175                 180                 185 tac atg atc gtg atc ggc gtg atc atc ctg gcc gcc ctg ttc atg tac      628
Tyr Met Ile Val Ile Gly Val Ile Ile Leu Ala Ala Leu Phe Met Tyr
            190                 195                 200 tac gcc aag cgg atg ctg ttc acc agc acc aac gac aag atc aag ctg      676
Tyr Ala Lys Arg Met Leu Phe Thr Ser Thr Asn Asp Lys Ile Lys Leu
            205                 210                 215 atc ctg gcc aac aag gaa aac gtg cac tgg acc acc tac atg gac acc      724
Ile Leu Ala Asn Lys Glu Asn Val His Trp Thr Thr Tyr Met Asp Thr
        220                 225                 230 ttt ttc cgg acc agc ccc atg gtg atc gcc acc acc gac atg cag aac      772
Phe Phe Arg Thr Ser Pro Met Val Ile Ala Thr Thr Asp Met Gln Asn
235                 240                 245                 250 tgatgagagc tccagctttt gttccc                                         798

<210> SEQ ID NO 4
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Gly Ala Ala Ala Ser Ile Gln Thr Thr Val Asn Thr Leu Ser Glu
1               5                   10                  15

Arg Ile Ser Ser Lys Leu Glu Gln Glu Ala Asn Ala Ser Ala Gln Thr
            20                  25                  30

Lys Cys Asp Ile Glu Ile Gly Asn Phe Tyr Ile Arg Gln Asn His Gly
        35                  40                  45

Cys Asn Leu Thr Val Lys Asn Met Cys Ser Ala Asp Ala Asp Ala Gln
    50                  55                  60

Leu Asp Ala Val Leu Ser Ala Ala Thr Glu Thr Tyr Ser Gly Leu Thr
65                  70                  75                  80

Pro Glu Gln Lys Ala Tyr Val Pro Ala Met Phe Thr Ala Ala Leu Asn
                85                  90                  95

Ile Gln Thr Ser Val Asn Thr Val Arg Asp Phe Glu Asn Tyr Val
            100                 105                 110

Lys Gln Thr Cys Asn Ser Ser Ala Val Val Asp Asn Lys Leu Lys Ile
        115                 120                 125

Gln Asn Val Ile Ile Asp Glu Cys Tyr Gly Ala Pro Gly Ser Pro Thr
    130                 135                 140

Asn Leu Glu Phe Ile Asn Thr Gly Ser Ser Lys Gly Asn Cys Ala Ile
145                 150                 155                 160

Lys Ala Leu Met Gln Leu Thr Thr Lys Ala Thr Thr Gln Ile Ala Pro
                165                 170                 175

Lys Gln Val Ala Gly Thr Gly Val Gln Phe Tyr Met Ile Val Ile Gly
            180                 185                 190

Val Ile Ile Leu Ala Ala Leu Phe Met Tyr Tyr Ala Lys Arg Met Leu
        195                 200                 205

Phe Thr Ser Thr Asn Asp Lys Ile Lys Leu Ile Leu Ala Asn Lys Glu
    210                 215                 220

Asn Val His Trp Thr Thr Tyr Met Asp Thr Phe Phe Arg Thr Ser Pro
225                 230                 235                 240

Met Val Ile Ala Thr Thr Asp Met Gln Asn
                245                 250
```

```
<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5 gggggggctag catggacgga actcttttcc ccgg                                  34

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gggagatctt tactcatatg gacgccgtcc                                        30

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gggggagatc tatgggtgcc gcagcaagc                                         29

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gggctgcagt cagttttgca tatccg                                            26
```